US012630536B2

(12) United States Patent
Liu et al.

(10) Patent No.: US 12,630,536 B2
(45) Date of Patent: May 19, 2026

(54) CYANOTRIAZINE DERIVATIVE, PREPARATION METHOD THEREFOR, AND APPLICATION THEREOF

(71) Applicant: Chengdu Fanxi Biopharma Co., LTD., Sichuan (CN)

(72) Inventors: Xiaoyu Liu, Sichuan (CN); Niefang Yu, Sichuan (CN); Xin Chen, Sichuan (CN); Hao Li, Sichuan (CN)

(73) Assignee: Chengdu Fanxi Biopharma Co., LTD., Chengdu Sichuan (CN)

( * ) Notice: Subject to any disclaimer, the term of this patent is extended or adjusted under 35 U.S.C. 154(b) by 536 days.

(21) Appl. No.: 18/041,743

(22) PCT Filed: Aug. 18, 2021

(86) PCT No.: PCT/CN2021/113269

§ 371 (c)(1),
(2) Date: Feb. 15, 2023

(87) PCT Pub. No.: WO2022/037617

PCT Pub. Date: Feb. 24, 2022

(65) Prior Publication Data

US 2023/0312527 A1 Oct. 5, 2023

(30) Foreign Application Priority Data

Aug. 19, 2020 (CN) ......................... 202010841183.5

(51) Int. Cl.

| | |
|---|---|
| ***C07D 403/10*** | (2006.01) |
| ***A61K 31/53*** | (2006.01) |
| ***A61P 1/16*** | (2006.01) |
| ***A61P 3/00*** | (2006.01) |
| ***A61P 3/04*** | (2006.01) |
| ***A61P 3/06*** | (2006.01) |
| ***A61P 3/14*** | (2006.01) |
| ***A61P 5/14*** | (2006.01) |
| ***A61P 9/00*** | (2006.01) |
| ***A61P 9/10*** | (2006.01) |
| ***A61P 35/00*** | (2006.01) |
| ***C07D 403/12*** | (2006.01) |
| ***C07D 403/14*** | (2006.01) |

(52) U.S. Cl.

CPC .............. *C07D 403/12* (2013.01); *A61P 3/06* (2018.01); *C07D 403/10* (2013.01)

(58) Field of Classification Search

CPC ................ C07D 403/10; C07D 403/12; C07D 403/14; A61K 31/53; A61P 1/16; A61P 3/00; A61P 3/04; A61P 3/06; A61P 3/14; A61P 5/14; A61P 9/00; A61P 9/10; A61P 35/00

See application file for complete search history.

(56) References Cited

U.S. PATENT DOCUMENTS

| | | | | |
|---|---|---|---|---|
| 6,787,652 B1 | | 9/2004 | Dow et al. | |
| 12,338,206 B2 | * | 6/2025 | Zhang | A61P 3/06 |
| 2022/0281849 A1 | * | 9/2022 | Kirschberg | C07D 413/12 |
| 2024/0059682 A1 | * | 2/2024 | Kirschberg | A61P 3/00 |

FOREIGN PATENT DOCUMENTS

| | | | |
|---|---|---|---|
| CN | 1389203 | A | 1/2003 |
| CN | 108727344 | A | 11/2018 |
| CN | 110938094 | A | 3/2020 |
| WO | 2009037172 | A1 | 3/2009 |
| WO | 2020073974 | A1 | 4/2020 |
| WO | 2020169069 | A1 | 8/2020 |
| WO | 2021041237 | A1 | 3/2021 |
| WO | 2022187403 | A1 | 9/2022 |

OTHER PUBLICATIONS

Abel et al., Divergent Roles for thyroid hormone receptor β isoforms in the endocrine axis and auditory system. Journal Clinical Invest., 1999, vol. 104, pp. 291-300.

Jones et al., Lipoprotein subclasses and their associations with physical activity, cardiorespiratory fitness and adiposity in Norwegian schoolchildren: the active smarter kids study. Preventive Cariology/ Lipids. P5386, 2018.

Kelly et al., Discovery of 2-[3,5-Dichloro-4-(5-isopropyl-6-oxo= 1,6-dihydropyridazin-3-yloxy)phenyl]-3,5-dioxo-2,3,4,5-tetrahydro[1,2]triazine-6carbonitrile (MGL-3196), a Highly Selective Thyroid Hormone Receptor B Agonist in Conical Trials for the Treatment of Dyslipidemia. Journal of Medicinal Chemistry, Drug Annotation, pubs.acs.org/jmc. Apr. 8, 2014. vol. 57, ppl. 3912-3923.

Saponaro et al., Selective Thyroid Hormone Receptor-Beta (TRβ) Agonists: New Perspecitves for the Treatment of Metabolic and Neurodegenerative Disorders; Frontiers in Medicine, Review, Jul. 9, 2020, Volum 7, Aritcle 331, pp. 1-14.

* cited by examiner

*Primary Examiner* — Brenda L Coleman

(74) *Attorney, Agent, or Firm* — Tracey S. Truitt; Sandberg Phoenix & von Gontard, PC

(57) ABSTRACT

A compound represented by structural formula (I) and a pharmaceutically acceptable salt thereof and a pharmaceutical composition comprising the compound or the pharmaceutically acceptable salt thereof, can be used for treating diseases such as obesity, hyperlipidemia, hypercholesterolemia, and diabetes and also for treating other diseases such as NASH, atherosclerosis, cardiovascular diseases, hypothyroidism, thyroid cancer and other related disorders and diseases a (I)

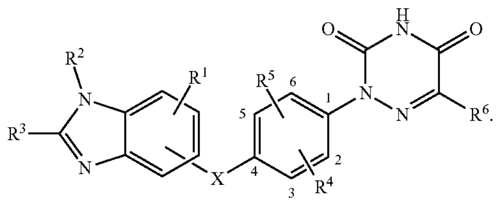

7 Claims, 2 Drawing Sheets

CYANOTRIAZINE DERIVATIVE, PREPARATION METHOD THEREFOR, AND APPLICATION THEREOF

CROSS-REFERENCE TO RELATED APPLICATIONS

The present application is a U.S. National Application based on International Patent Application No. PCT/CN2021/113269, filed Aug. 18, 2021, which claims priority to CN Application No. 202010841183.5, filed Aug. 19, 2020, both of which are incorporated by reference in their entireties.

TECHNICAL FIELD

The present invention relates to a subtype agonist derivative of a thyroid hormone receptor-β (THR-beta), its preparation method and medical use. The derivative of the present invention or a pharmaceutical composition containing the derivative of the present invention may be used for treating related diseases, for example, may be used for treating obesity, hyperlipidemia, hypercholesterolemia, diabetes, and the like; and may also be used for treating other diseases, comprising NASH (nonalcoholic steatohepatitis), hepatic steatosis, atherosclerosis, cardiovascular diseases, hypothyroidism, thyroid cancer and other related diseases.

BACKGROUND

Thyroid hormone plays a key role in normal growth and development, and maintenance of metabolic balance (Physiological Reviews, 2001, 81(3), 1097-1042; Biochimica et Biophysica Acta 1812 (2011) 929-937). A circulating level of the thyroid hormone is closely regulated by a feedback mechanism in hypothalamus/pituitary/thyroid axis. Thyroid dysfunction may lead to hypothyroidism or hyperthyroidism. In addition, the thyroid hormone also has a very important influence on heart function, weight, metabolism, metabolic rate, body temperature, cholesterol, bone, muscle and behavior.

Thyroid hormone is produced by a thyroid and secreted into a circulatory system in two different forms: 3,5,3',5'-tetra-iodine-L-thyronine (T4) and 3,5,3'-tri-iodine-L-thyronine (T3). T4 is a main form of secretion of the thyroid. T3 is a physiologically more active form of existence. T4 may be converted into T3 through a tissue-specific deiodinase. This tissue-specific deiodinase exists in all tissues, but mainly exists in liver and kidney. A biological activity of the thyroid hormone is mediated by thyroid hormone receptors (THRs) (Endocrine Reviews, 1993, 348-399). THR belongs to a superfamily known as a nuclear receptor. Main thyroid receptor subtypes comprise: α1, α2, β1 and β2. The thyroid hormone receptors α1, α1 and β2 may directly bind to the thyroid hormone T3, while α2 may interact with non-T3 (Advances in Developmental Biology. 2006, 16, 1-31). Studies have shown that the thyroid hormone receptor subtypes may be different in their contributions to special physiological response. For example, THR-β1 plays an important role in regulating a TRH (thyrotropin releasing hormone) and the thyroid hormone in liver. THR-β2 plays a major role in regulating a TH (thyroid stimulating hormone). THR-β1 plays an important role in regulating a heart rate. For example, the thyroid hormone increases a metabolic rate, oxygen consumption and heat release. Therefore, the weight is decreased. The weight decrease may bring beneficial effects to a patient with obesity by improving comorbidity related to obesity, and may also bring beneficial effects on blood glucose control of a patient with obesity suffering from type-2 diabetes (J. Clin. Invest., 1999, 104: 291-300).

Obviously, a corresponding biological function may be changed by activating THR-β1, so as to achieve some expected therapeutic purpose. In view of increasing incidence rates of the obesity and diseases caused by the obesity, comprising, but not limited to diabetes, metabolic syndrome and atherosclerotic vascular diseases, the society is in urgent need of a compound capable of treating these diseases. Therefore, a thyroid hormone analogue with an improved selective and/or tissue selective action of the thyroid hormone receptor β is attracting wide attention. This THR-β selective agonist may cause appropriate decreases of body weight, lipids, cholesterol and some lipoproteins, and has an effect of decrease on a cardiovascular function or a normal function of hypothalamus/pituitary/thyroid axis (J. Med. Chem. 2014, 57, 3912-3923; Expert Opin Investig Drugs. 2004, 13(5):489-500).

MGL-3196 (I) of Madrigal Pharmaceuticals selectively acts on THR-β, with an obvious effect on a patient with nonalcoholic steatohepatitis (NASH) and little side effects on liver, and is a safe lipid-lowering (LDL, LDL-C and TG) drug, which is currently in a key development stage of clinical trial (J. Med. Chem. 2014, 57, 3912-3923). F. Hoffmam-La Roche Company introduced a substituent at a 2-position of pyridazinone to obtain a series compound II. The compound II not only has a function of treating the NASH, but also has a function of resisting thyroid cancer (WO2009037172A1). A substituent introduced at a 2-position of pyridazinone by Sichuan Haisco Pharmaceutical Co., Ltd. is an ether substituent, and a corresponding derivative III may be used for treating obesity, hyperlipidemia, hypercholesterolemia, diabetes and other related diseases (CN110938094A). Jiaxing TechnoDerma Medicines Inc. invented IV, which might be used for treating androgenetic alopecia or seborrheic alopecia or alopecia caused by chemotherapy (CN108727344A).

I

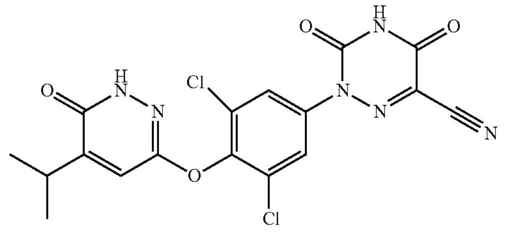

MGL-3196

II

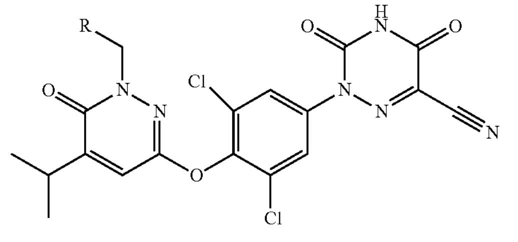

(WO2009037172A1)

-continued

III

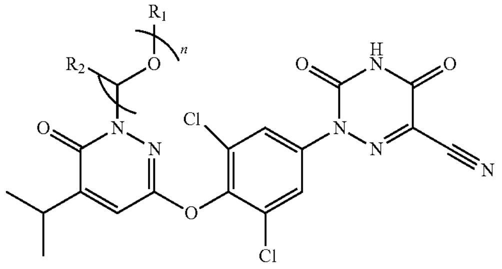

(WO2009037172A1)

IV

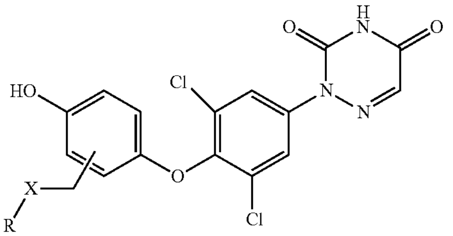

(CN108727344A)

The selective agonist of THR-β, represented by MGL-3196, can significantly reduce liver fat and fibrosis degrees of the patient with NASH, and can also significantly reduce LDL cholesterol, triglyceride, lipoprotein, and the like at the same time. Therefore, the selective agonist of THR-β has become an ideal candidate drug for reducing cardiovascular risks of the patient with NASH and a patient with dyslipidemia suffering from intolerance to moderate dose of statins or statins (European Heart Journal, Volume 39, Issue suppl_1, 1 Aug. 2018, 566. P5387).

Since a physiological function of the thyroid hormone affects almost every organ system, it is still necessary to further improve the absorption, distribution, transportation and metabolism of drug in vivo, and improve a bioavailability and a selectivity of drug to a target site, so as to enhance a therapeutic effect, reduce toxic and side effects of drug, and prolong an action time, thus meeting social needs and better benefiting mankind.

SUMMARY

A compound represented by general structural formula (I) or a pharmaceutically acceptable salt, a polymorph, a tautomer, a stereoisomer, a hydrate, a solvate or any isotope derivative thereof:

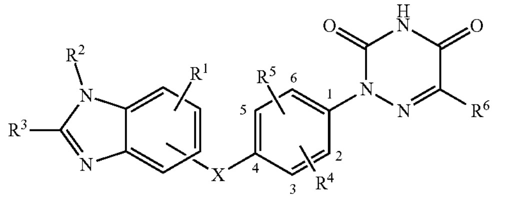

general structural formula (I)

wherein, $R^1$ is selected from: H, —CN, —$NO_2$, —$CF_3$, —$OCF_3$, —$CO_2H$, —OH, ethynyl, halogen, amino, alkyl, alkenyl, haloalkyl, haloalkenyl, heteroalkyl, heterocycloalkyl, arylalkyl, cycloalkyl, aryl, heterocycloaryl, heterocycloaryllalkyl, heterocycloalkyl, hetercycloalkenyl, alkoxy, alkoxyalkyl, alkenyloxy, alkynyl, alkylalkynyl, alkynyloxy, alkylalkynyloxy, alkynyloxy, amino, alkylamino, aminoalkyl, alkylaminocarbonyl, sulfonyl, alkylsulfonyl, alkylsulfinyl, aminosulfonyl, and acyl; and in the groups above, each can be unsubstituted or substituted by one or more substituents, and the substituents comprise: halogen, —$CF_3$, alkyl, alkenyl, alkynyl, hydroxyl, hydroxyalkyl, alkoxy, alkoxyalkyl, amino, alkylamino, and cycloalkylamino.

$R^2$ is selected from: H, alkyl, alkenyl, haloalkyl, haloalkenyl, heteroalkyl, heterocycloalkyl, arylalkyl, cycloalkyl, aryl, heterocycloalkyl, heterocycloarylalkyl, heterocycloalkyl, heterocycloalkenyl, alkoxy, alkoxyalkyl, alkylamino, alkylaminocarbonyl, alkynyl, alkylalkynyl, -alkynyloxy, -alkylalkynyloxy, sulfonyl, alkylsulfonyl, alkylsulfinyl, and aminosulfonyl; and in the groups above, each can be unsubstituted or substituted by one or more substituents, and the substituents comprise: halogen, —$CF_3$, alkyl, alkenyl, alkynyl, hydroxyl, hydroxyalkyl, alkoxy, alkoxyalkyl, amino, alkylamino, and cycloalkylamino.

$R^3$ is selected from: H, —CN, —$NO_2$, —$CF_3$, —$OCF_3$, —$CO_2H$, —OH, —$SR^7$, halogen, amino, alkyl, alkoxy, alkoxyalkyl, heteroalkyl, heterocycloalkyl, arylalkyl, cycloalkyl, heterocycloarylalkyl, heterocycloalkyl, heterocycloalkenyl, alkenyloxy, alkynyl, alkylalkynyl, alkynyloxy, alkylalkynyloxy, alkylamino, aminoalkyl, and alkylaminocarbonyl; and in the groups above, each can be unsubstituted or substituted by one or more substituents, and the substituents comprise: halogen, —$CF_3$, alkyl, alkenyl, alkynyl, hydroxyl, hydroxyalkyl, alkoxy, alkoxyalkyl, amino, alkylamino, and cycloalkylamino.

$R^4$ and $R^5$ are each selected from: H, halogen, alkyl, alkoxy, and alkoxyalkyl.

$R^6$ is selected from: H, —CN, —$NO_2$, —$CF_3$, —$OCF_3$, —$CO_2H$, —OH, alkyl, halogen, carboxyl, ester, and amide.

X is selected from: covalent bond, —O—, —S—, —NH—, —$SO_2$—, —CONH—, or —$(CH_2)q$-, X— is attached to carbon atoms on C4-, C5-, C6- and C7-positions of a benzimidazole ring, and q is 1, 2, or 3.

In some specific embodiments, $R^1$ is preferably: H, halogen, and C1-C4 alkyl.

In another specific embodiment, $R^2$ is preferably: H, and C1-C4 alkyl.

In another specific embodiment, $R^3$ is preferably: H, halogen, and C1-C6 alkyl.

In another specific embodiment, X is preferably: —O—.

In another specific embodiment, $R^4$ and $R^5$ are each Br preferably, wherein $R^4$ and $R^5$ are respectively attached to $C_3$- and $C_5$-positions on a corresponding benzene ring.

In another specific embodiment, $R^4$ and $R^5$ are each Cl preferably, wherein $R^4$ and $R^5$ are respectively attached to $C_3$- and $C_5$-positions on a corresponding benzene ring.

In another specific embodiment, R6 is preferably: —CN.

In addition to the compound represented by general structural formula (I), the present invention further comprises a pharmaceutically acceptable salt, a polymorph, a tautomer, a stereoisomer, a hydrate, a solvate or an isotope derivative, a pharmaceutically acceptable prodrug and a pharmaceutically active metabolite of the compound, and a pharmaceutically acceptable salt of the metabolite.

The present invention comprises any pharmaceutical dosage form formed by a compound represented by general structural formula (I) and a pharmaceutically acceptable diluent, excipient or vector.

The present invention also relates to a method for preparing the compound. The compound may be used as a selective and/or tissue selective agonist of a thyroid hormone receptor β, which can produce a suitable decrease in body weight, lipids, cholesterol and lipoprotein, and have a decreased effect on cardiovascular functions or normal functions of hypothalamus/pituitary/thyroid axis. The compound may be used to treat metabolic diseases such as obesity, hyperlipidemia, hypercholesterolemia, diabetes and other disorders and diseases such as hepatic steatosis and NASH, atherosclerosis, cardiovascular diseases, hypothyroidism, thyroid cancer, thyroid diseases, and related disorders and diseases.

In another specific embodiment, the compound represented by general structural formula (I) may treat diseases such as various lipid abnormalities, metabolic syndrome, obesity, atherosclerosis or diabetes.

In another specific embodiment, the compound represented by general structural formula (I) may treat diseases such as NASH and Duchenne muscular dystrophy.

In another specific embodiment, the compound represented by general structural formula (I) may treat diseases such as primary biliary cirrhosis and cholangitis, comprising senile dementia and tumors.

In another specific embodiment, the compound represented by general structural formula (I) may treat diseases such as increasing energy and activation performances of T lymphocytes to enhance immune functions, and transforming tumor cells into fat cells, and reducing cancer metastasis.

In another specific embodiment, the compound represented by general structural formula (I) may treat visceral fat obesity.

In another specific embodiment, the compound represented by general structural formula (I) may treat thyroid diseases, comprising thyroid cancer.

One or more embodiments of the present application further provide a method for treating and/or preventively treating a disease regulated by a thyroid hormone. The method comprises administering the compound according to the present application to a subject in need thereof.

One or more embodiments of the present application further provide a method for treating and/or preventively treating obesity, diabetes, NASH, cardiovascular diseases, hypothyroidism, or thyroid cancer regulated by a thyroid hormone. The method comprises administering the compound according to the present application to a subject in need thereof.

One or more embodiments of the present application further provide a method for treating and/or preventively treating hyperlipidaemia or atherosclerosis regulated by a thyroid hormone. The method comprises administering the compound according to the present application to a subject in need thereof.

One or more embodiments of the present application further provide a method for treating and/or preventively treating hypercholesterolemia regulated by a thyroid hormone. The method comprises administering the compound according to the present application to a subject in need thereof.

One or more embodiments of the present application further provide a compound for treating and/or preventively treating a disease regulated by a thyroid hormone.

One or more embodiments of the present application further provide a compound for treating and/or preventively treating obesity, diabetes, NASH, cardiovascular diseases, hypothyroidism, or thyroid cancer regulated by a thyroid hormone.

One or more embodiments of the present application further provide a compound for treating and/or preventively treating hyperlipidemia or atherosclerosis regulated by a thyroid hormone.

One or more embodiments of the present application further provide a compound for treating and/or preventively treating hypercholesterolemia regulated by a thyroid hormone.

EMBODIMENTS

Definitions

Figure 1:
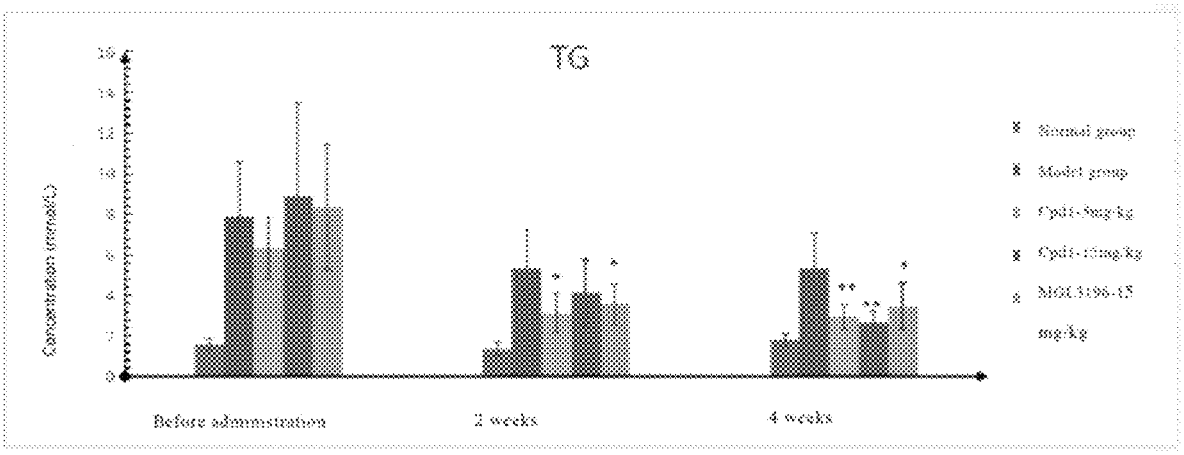
FIG. 1 shows test results of blood TG (triglyceride) indexes in an in-vivo pharmacodynamic test.

As used herein, the term "the compound of the present invention" refers to the compound represented by general structural formula (I). The term further comprises various crystal forms, pharmaceutically acceptable salts, hydrates or solvates of the compound of formula (I).

As used in the present invention, the term "unsubstituted" means no substituents or being only substituted by hydrogen.

Some terms used in the present invention are defined as follows:

"Halogen" refers to fluorine, chlorine, bromine and iodine.

"Alkyl", when regarded as a group or a part of a group, means a linear or branched aliphatic hydrocarbon group. The alkyl is preferably C1-C14 alkyl; more preferably C1-C10 alkyl; and most preferably C1-C6 alkyl unless otherwise specified. Examples of the linear or branched C1-C6 alkyl include, but are not limited to, methyl, ethyl, n-propyl, 2-propyl, n-butyl, isobutyl, tert-butyl, hexyl, and the like.

"Alkylamino" comprises monoalkylamino and dialkylamino, unless otherwise specified. "Monoalkylamino" refers to: -(alkyl-NH)— group; and "dialkylamino" refers to: $-((alkyl)_2N)$— group. See related definition herein for the alkyl. The alkyl group may be preferably C1-C6 alkyl group. Examples comprise, but are not limited to, N-methylamino, N-ethylamino, N-isopropylamino, N,N-(diethyl)amino, and the like.

"Aminoalkyl" refers to: -(amino-alkyl)- group. See related definition herein for the alkyl. Examples comprise, but are not limited to, aminoethyl, 1-aminopropyl, 1-aminopropyl, and the like.

"Arylamino" comprises both mono-arylamino and di-arylamino, unless otherwise specified. The mono-arylamino refers to: -(aryl-)NH— group; and the di-arylamino refers to $-(alkyl)_2N$— group. See related portion herein for the definition of the aryl.

"Acyl" comprises a -(alkyl-CO)— group and a -(aryl-CO)— group, unless otherwise specified. See related definitions for the alkyl or the aryl herein. Examples of acyl comprise, but are not limited to, acetyl, propionyl, isobutyryl, benzoyl, and the like.

"Acylamino" comprises an -(alkyl-CONH)— group and an -(aryl-CONH) group-, unless otherwise specified. See related portion herein for the definition of alkyl or aryl. Examples of the acylamino comprise, but are not limited to, acetamido-, propionamido-, butamido-, isobutamido-, benzamido-, and the like.

"Alkenyl", as a group or part of a group, refers to an aliphatic hydrocarbon group containing at least one carbon-carbon double bond, the hydrocarbon group may be linear or branched. An C2-C14 alkenyl is preferred. An C2-C12 alkenyl is more preferred; and an C2-C6calkenyl is most preferred. The group may contain a plurality of double bonds in the main chain thereof and the conformation of the double bonds may each be E or Z. Examples of the alkenyl group comprise, but are not limited to, vinyl, propenyl, and the like.

"Alkoxy" refers to an -(alkyl-O)— group. See related definition herein for the alkyl. C1-C6 alkoxy is preferred. Examples of alkoxy comprise, but are not limited to, methoxy, ethoxy, n-propoxy, isopropoxy, n-butoxy, isobutoxy, and the like.

"Alkenyloxy" refers to an -(alkenyl-O)— group. See related definition herein for alkenyl. C1-C6 alkenyloxy is preferred.

"Alkynyloxy" refers to an -(alkynyl-O)— group. See related definition herein for the alkynyl. C1-C6 alkynyloxy is preferred.

"Alkoxycarbonyl" refers to an -(alkyl-O—C(O))— group. See related definition herein for alkyl. A preferable alkyl group is C1-C6 alkyl. Examples of alkoxycarbonyl comprise, but are not limited to, methoxycarbonyl, ethoxycarbonyl, and the like.

"Alkylsulfinyl" refers to an -(alkyl-S(O))— group. See related definition herein for alkyl. A preferable alkyl is C1-C6 alkyl group. Examples of alkylsulfinyl group comprise, but are not limited to, methylsulfonyl, ethylsulfinyl, and the like.

"Alkylsulfonyl" refers to an -(alkyl-$S(O)_2$—O)— group. See related definition herein for alkyl. The alkyl may be preferably C1-C6 alkyl group. Examples of alkylsulfonyl comprise, but are not limited to, methylsulfonyl, ethylsulfonyl, and the like.

"Alkylaminocarbonyl" refers to an alkylamino-carbonyl group. See related definitions herein for the alkylamino.

"Cycloalkyl" refers to saturated or partially saturated monocyclic, fused, or spirocyclic carbocycles. A ring composed of 3 to 9 carbon atoms is preferably selected. Examples comprise, but are not limited to, cyclopropyl, cyclobutyl, cyclopentyl, cyclohexyl, and the like.

"Cycloalkylalkyl" refers to a cycloalkyl-alkyl group. See related definitions herein for cycloalkyl and alkyl. Monocycloalkylalkyl groups comprise, but are not limited to, cyclopropyl methyl, cyclopentyl methyl, cyclohexyl methyl, cycloheptyl methyl, and the like.

"Heterocycloalkyl" refers to a cycloalkyl containing at least one heteroatom selected from N, S and O. The heterocycloalkyl preferably contains 1 to 3 (1, 2 or 3) heteroatoms. A preferred ring is a 3-14 membered ring, and a more preferred ring is a 4-7 membered ring. The heterocycloalkyl comprises, but is not limited to, pyrrolidinyl, dihydropyrrolyl, tetrahydropyrrolyl, dihydropyrazolyl, piperidinyl, morpholintetrahydrofuryl, tetrahydrothiofuryl, tetrahydropyranyl, and the like.

"Heterocycloalkenyl" refers to a heterocycloalkyl containing at least one double bond. See related definition herein for the heterocycloalkyl.

"Heterocycloalkylalkyl" refers to a -(heterocycloalkyl-alkyl)- group. See related definitions herein for heterocycloalkyl and alkyl. The heterocycloalkylalkyl group comprises, but is not limited to, (2-tetrahydrofuryl)methyl, (2-tetrahydrothiofuryl)methyl, and the like.

"Heteroalkyl" refers to a linear or branched alkyl group, and containing at least one or more (for example, 1, 2 or 3) heteroatoms selected from S, O and N in its main chain. The heteroalkyl preferably contains 2 to 14 atomic chains. The heteroalkyl comprises, but is not limited to, ethers, thioethers, alkyl esters, second or third alkyl amines, alkyl sulfinic acids, and the like.

"Aryl", as a group or part of a group refers to: (1) aromatic monocyclic or fused ring; aromatic carbocyclic ring with 5-12 carbon atoms (ring structure in which all ring atoms are carbon) is preferred. Examples of the aryl comprise, but are not limited to, phenyl and naphthyl; (2) a partially saturated carbocyclic ring can be attached, for example, phenyl and C5-7 cycloalkyl or C5-7 cycloalkenyl groups are fused to each other to form a cyclic structure. Examples comprise, but are not limited to, tetrahydronaphthyl, indenyl or hydroindenyl, and the like. The aryl group may be substituted with one or more substituents.

"Arylalkenyl" refers to: an -(aryl-alkenyl)- group. See related definitions for aryl and alkenyl herein. Exemplary arylalkenyl groups comprise, but are not limited to, phenylpropenyl and the like.

"Arylalkyl" refers to: an -(aryl-alkyl)- group. See related definitions for aryl and the alkyl herein. Exemplary arylalkyl groups comprise, but are not limited to, benzyl, phenethyl, 1-menaphthyl, and the like.

"Cycloalkenyl" refers to a non-aromatic monocyclic or multicyclic ring system, which contains at least one carbon-carbon double bond and preferably has 5 to 10 carbon atoms per ring. Exemplary monocyclic cycloalkenyl rings comprise, but are not limited to, cyclopentene, cyclohexene, or cycloheptene. The cycloalkenyl group may be substituted with one or more substituents.

"Heteroaryl" refers to monocyclic or fused polycyclic aromatic heterocycle. A 5-7 membered aromatic ring containing one or more (for example, 1, 2 or 3) heteroatoms selected from N, O or/and S is preferred. Typical heteroaryl substituents comprise, but are not limited to, furyl, thienyl, pyrrole, pyrazole, triazole, thiazole, pyridine, pyrimidine, pyrazine, indole, benzimidazole, and the like.

"Heteroarylalkyl" refers to: a -(heteroaryl-alkyl)- group. See related definitions for heteroaryl and alkyl herein. Exemplary heteroarylalkyl groups comprise, but are not limited to, 2-furfuryl, 3-furfuryl, 2-picolyl, and the like.

The present invention comprises the compound represented by general structural formula (I) and various possible isomeric forms thereof. The compound comprises: diastereoisomers, enantioisomers, tautomers, geometric isomers of "E" or "Z" configuration isomers, and the like. Any chemist with a certain basis can isolate the above optically pure or stereoisomerically pure compound.

The present invention comprises the compound represented by general structural formula (I) and possible mixtures of racemates and/or enantioisomers and/or diastereoisomers thereof.

In addition, use of the compound represented by general structural formula (I) also covers solvated and non-solvated forms of the compound. Therefore, all the formulas comprise the compound with the specified structure, comprising hydrates, solvates and various forms of anhydrous compounds.

Use of the compound represented by general structural formula (I) according to the present invention also covers various crystal forms and amorphous forms of the compound. Therefore, the various crystal forms above comprise, but are not limited to, various hydrate crystal forms, various solvate crystal forms, various anhydrous compound crystal forms, and the like.

As used herein, the term "pharmaceutically acceptable salt" refers to those salts which are, within the scope of sound medical judgment, suitable for contact with tissues of humans and lower animals without excessive toxicity, irritation, allergic response, and the like, and are commensurate with a reasonable benefit/risk ratio. The pharmaceutically acceptable salt is well known in the art. For example, the pharmaceutically acceptable salt is described in detail by Berge et al, in J. Pharmaceutical Sciences (1977) 66: 1-19. The pharmaceutically acceptable salt of the compound of the present invention comprises those salts derived from suitable inorganic and organic acids and inorganic and organic bases. Examples of pharmaceutically acceptable nontoxic acid addition salts are salts formed with inorganic acids such as hydrochloric acid, hydrobromic acid, phosphoric acid, sulfuric acid and perchloric acid, or salts formed with organic acids such as acetic acid, oxalic acid, maleic acid, tartaric acid, citric acid, succinic acid or malonic acid; and also comprise salts formed using methods conventional in the art, for example, ion exchange method. Other pharmaceutically acceptable salts comprise: hexanedioic acid salts, alginates, ascorbates, aspartates, benzene sulfonates, benzoates, bisulfates, borates, butyrates, camphorates, camphorsulfonates, citrates, cypionates, digluconates, lauryl sulfates, ethanesulfonates, formates, fumarates, gluconates, glycerophosphates, gluconates, hemisulfates, heptanoates, caproates, hydroiodates, 2-hydroxylethanesulfonates, lactonates, lactates, lauroleates, lauryl sulfates, malates, maleates, malonates, mesylates, 2-naphthalenesulfonates, nicotinates, nitrates, oleates, oxalates, palmitates, dihydroxynaphthalenes, pectates, persulfates, 3-phenpropionates, phosphates, picrates, pivalates, propionates, stearates, succinates, sulfates, tartrates, thiocyanates, p-toluenesulfonates, undecanoates, valeratse, and the like. The pharmaceutically acceptable salts derived from suitable bases comprise alkali metals, alkali earth metals, ammonium and N+(C1-4alkyl)4 salts. Representative alkali metals or alkali earth metal salts comprise sodium, lithium, potassium, calcium, and magnesium salts, and the like. Other pharmaceutically acceptable salts comprise, if appropriate, nontoxic ammonium, quaternary ammonium and amine cations formed with counterions such as halide ions, hydroxide, carboxylate, sulfate, phosphate, nitrate, lower-grade alkyl sulfonate and aryl sulfonate.

The term "solvate" refers to a complex of the compound of the present invention coordinated to solvent molecules in a specific ratio. The "solvate" refers to a complex of the compound of the present invention coordinated to water.

The compound of the present invention may comprise one or more asymmetric centers, and thus may have a plurality of "stereoisomer" forms, for example, enantiomer and/or diastereomer forms. For example, the compound of the present invention may be individual enantiomers, diastereomers or geometric isomers (e.g., cis and trans isomers), or may be in the form of mixtures of stereoisomers, comprising racemic mixtures and mixtures rich in one or more stereoisomers. The isomers can be separated from the mixture by methods known to those skilled in the art. The methods comprise: chiral high pressure liquid chromatography (HPLC) and chiral salt formation and crystallization; or, preferred isomers may be prepared by asymmetric synthesis.

The pharmacological effects may be embodied by, but are not limited to, the following descriptions.

A ligand binding domain of THR-β (amino acids 148-410) (H6-THR-β) and a ligand binding domain of THR-α (amino acids 202-461) (H6-TRα) were cloned into *E. coli* expression vector pET28a (Novagen, Milwaukee, Wis.) containing N-terminal six His sequences. The resulting recombinant six-His-tagged protein was produced in *E. coli* BL21(DE3) cells. The cells were grown in Terrific Broth (self-used self-prepared Bacto tryptone (3.3%, w/v), Difico yeast extract (2.0%, w/v) and NaCl (0.5%, w/v) medium), incubated at 25° C. for 24 hours using a shake flask in 0.2 mM IPTG, harvested or dissolved with 5 volumes of buffer A (0.05 M Tris, 0.3 M NaCl, 1% W/V betaine, 0.01 M imidazole, 0.02 M b-mercaptoethanol, pH 8.0). Lysozyme (1.0 mg/ml, Sigma) and CompleteProtease Inhibitor Cocktail (Roche Diagnostics Gmbh) were added to the slurry and the solution was sonicated for one minute and 5 times at 4° C. The suspension was centrifuged at 127,300 RCF for 2 hours in a Ti45 Beckmann rotor and the supernatant was loaded onto an NI NTAAgarose (Quigen 30210) column. After washing with the buffer A, 116-THR-β or H6-THR-α was eluted with the buffer A containing 0.25 M imidazole.

30 microliters of H6-THR-β (50 nM) or H6-THR-α in 50 mM Hepes, pH 7.0, 1 mM DTT, 0.05% NP40 and 0.2 mg/ml BSA (binding buffer) were mixed with an equal volume of EE-RxRα (50 nM) in the binding buffer. 6 microliters of T3 (0-14.8 uM) or test compound (0-1.2 mM) in DMSO were added and the solution was incubated at 37° C. for 30 minutes. 30 microliters of biotin-GRIP peptide (biotin-Aca-HGTSLKEKHKILHRLLQDSSSPVDL-CONH2) (100 nm) in 30 μl of binding buffer plus 5% DMSO were added, and the solution was incubated at 37° C. for 30 minutes. 30 microliters of a solution containing 12 nM europium-conjugated anti-six His antibody and 160 nM APC-conjugated streptavidin in 50 mM Tris, pH 7.4, 100 mM NaCl and 0.2 mg/ml BSA were added and the solution was incubated overnight at 4° C. Aliquot (35 μm/sample) was transferred to a 384-well black microtiter plate. HTRF signal was read on a Victor5 reader (PerkinElmer Life and Analytical Sciences). EC50 was calculated.

The term "prodrug" comprises a kind of compound, which may be biologically active or inactive, and after being subjected to metabolism or chemical reaction in a human body after being taken by appropriate methods, can be converted to formula (I), or a salt or solution composed of the compound of formula (I). The prodrug comprises (but is not limited to) carboxylate, carbonate, phosphate, nitrate, sulfate, sulfone ester, sulfoxide, amino compound, carbamate, azo compound, phosphamide, glucoside, ether, acetal and other forms of the compound.

The term "subject" as used herein comprises, but is not limited to, a human (i.e., a male or female of any age group, e.g., a pediatric subject (e.g., an infant, a child, an adolescent) or an adult subject (e.g., a young adult, a middle-aged adult, or an older adult)) and/or a non-human animal, e.g., a mammal, e.g., a primate (e.g., a cynomolgus monkey, a rhesus monkey), a cow, a pig, a horse, a sheep, a goat, a rodent, a cat, and/or a dog. In some embodiments, the subject is a human. In some other embodiments, the subject is a non-human animal.

As used herein, unless otherwise specified, the term "treatment" comprises effects that occur when a subject suffers from a particular disease, disorder or condition, which reduces the severity of the disease, disorder or condition, or delays or slows the progression of the disease, disorder or condition ("therapeutic treatment"), and also comprises effects that occur before the subject begins to suffer from the particular disease, disorder or condition ("prophylactic treatment").

"Combination" and related terms refer to the simultaneous or sequential administration of the therapeutic agents of the present invention. For example, the compound of the present invention may be administered simultaneously or sequentially with another therapeutic agent in a separate unit dosage form, or simultaneously with another therapeutic agent in a single unit dosage form.

"Pharmaceutically acceptable excipient" refers to a non-toxic vector, adjuvant, or vehicle that does not destroy a pharmacological activity of the compound formulated together. The pharmaceutically acceptable vectors, adjuvants or vehicles that may be used in the composition of the present invention comprise, but are not limited to, ion exchangers, alumina, aluminum stearate, lecithin, serum proteins (such as human serum albumin), buffer substances (such as phosphates), glycine, sorbic acid, potassium sorbate, partial glyceride mixtures of saturated vegetable fatty acids, water, salts or electrolytes (such as protamine sulfate), disodium hydrogen phosphate, potassium hydrogen phosphate, sodium chloride, zinc salts, silica gel, magnesium trisilicate, polyvinylpyrrolidone, cellulose-based substances, polyethylene glycol, sodium carboxymethylcellulose, polyacrylates, waxes, polyethylene-polyoxypropylene-block polymers, polyethylene glycol and wool fat.

Administration modes of the compound or the pharmaceutical composition of the present invention are not particularly limited, and representative administration modes comprise (but are not limited to): oral administration, duodenal administration, rectal administration, parenteral administration (intravenous administration, intramuscular administration or subcutaneous administration) and local administration.

Solid dosage forms for oral administration comprise capsules, tablets, pills and granules. In these solid dosage forms, an active compound is mixed with at least one conventional inert excipient (or vector), such as sodium citrate or dicalcium phosphate, or mixed with the following ingredients: (a) fillers or solubilizers, such as starch, lactose, sucrose, glucose, mannitol and silicic acid; (b) binders, such as hydroxymethyl cellulose, alginate, gelatin, polyvinyl pyrrolidone, sucrose and arabic gum; (c) humectants, such as glycerine; (d) disintegrants, such as agar, calcium carbonate, potato starch or tapioca starch, alginic acid, some complex silicates, and sodium carbonate; (e) sustained-release solvents, such as paraffin; (f) absorption accelerators, such as quaternary ammonium compounds; (g) wetting agents, such as cetyl alcohol and glyceryl monostearate; (h) adsorbents, such as kaolin; and (i) lubricants such as talc, calcium stearate, magnesium stearate, solid polyethylene glycol, sodium dodecyl sulfate, or mixtures thereof. In the capsules, the tablets and the pills, the dosage forms may also contain buffers.

Solid dosage forms such as tablets, dragees, capsules, pills, and granules may be prepared using coatings and shells such as enteric coatings and other materials well known in the art. The solid dosage forms may contain opacifying agents and the release of the active compound or compound in such a composition may be delayed in release in a certain part of a digestive tract. Examples of embedding components which may be used are polymeric substances and wax-like substances. If necessary, the active compound may also be formed into microcapsules with one or more of the above excipients.

Liquid dosage forms for oral administration comprise pharmaceutically acceptable emulsions, solutions, suspensions, syrups or tinctures. In addition to the active compound, the liquid dosage forms may contain inert release agents conventionally employed in the art, such as water or other solvents, solubilizing agents and emulsifiers, for example, ethanol, isopropanol, ethyl carbonate, ethyl acetate, propylene glycol, 1,3-butylene glycol, dimethylformamide, and oils, in particular cotton seed oil, peanut oil, corn germ oil, olive oil, castor oil and sesame oil or mixtures of these substances.

The present invention provides a method for treating disorders related to diseases caused by THR-β in a subject in need thereof, which comprises the following steps of: administering the compound of the present invention or a pharmaceutically acceptable salt, a stereoisomer, a solvate, a hydrate, a crystal form, a prodrug or an isotope derivative thereof, or administering a pharmaceutical composition of the present invention to a subject in need thereof.

The compound of the present invention may be used for treating diseases caused by THR-β: any acute or chronic liver diseases involving pathological destruction, inflammation, degeneration and/or proliferation of liver cells, various lipid abnormalities and metabolic syndrome.

The present invention also relates to methods for preparing such compounds which may be used as selective and/or tissue selective agonists of THR-β, thereby producing a suitable reduction in body weight, lipids, cholesterol and lipoproteins, and having effects of reducing on cardiovascular function or normal function of hypothalamus/pituitary/thyroid axis. These compounds may be used to treat metabolic diseases such as obesity, hyperlipidemia, hypercholesterolemia, diabetes and other disorders and diseases such as hepatic steatosis and NASH, atherosclerosis, cardiovascular diseases, hypothyroidism, thyroid cancer, thyroid diseases, diabetes, NASH, Duchenne muscular dystrophy, and related diseases and diseases.

Preparation of Cyanotriazine Derivative

A compound represented by general structural formula (I) might be synthesized by the synthesis route and synthesis method discussed below. Used raw materials were conveniently and easily available. However, the synthesis route and the synthesis method used in the present invention might be widely applied in synthesis of an analogue, as long as initial raw materials were changed. For example, for synthesis of a compound not described in detail in an example herein, a needed target compound might be synthesized only by replacing the initial raw materials with starting raw materials of the corresponding target compound and changing reaction conditions slightly when necessary, according to the common sense of chemistry.

The synthesis route used in the present invention might also be applied to preparation of an intermediate or a target compound different from that in a specific embodiment. A reagent and/or an intermediate used might or might not be added with a protective group. A list of appropriate protective groups in organic synthesis might refer to Protective Groups in Organic Synthesis, Wiley, 2007 of G. M. Peter, or other reactions disclosed herein or known in the art.

The reagent capable of being used for synthesizing the target compound might be obtained or prepared according to the known art.

In the following examples, unless otherwise specified, all temperatures were in degrees Celsius.

All starting raw materials and reagents were commercially available. Suppliers comprised, but were not limited to, Aldrich Chemical Company, Lancaster Synthesis Ltd, and the like. The commercially available raw materials and reagents were all used directly without further purification, unless otherwise specified.

Glassware was dried in oven and/or dried by heating. A reaction was tracked on a glass silica gel-60 F254 plate (0.25 mm) (TLC). Analytical thin layer chromatography (TLC) was carried out by an appropriate solvent ratio (v/v). A moment when a starting material on the TLC was exhausted was used as a reaction end point (J. Org. Chem., Vol. 43, No. 14, 1978 2923-2925).

Generally, a volume of a reaction solution was doubled with a solvent used for the reaction in a subsequent treatment, and then extraction was carried out for three times with an extraction solvent which was 25% of total volume, unless otherwise specified. An extracted product was dehydrated with anhydrous sodium sulfate and filtered on a rotary evaporator, and the solvent was evaporated under a reduced pressure and removed in vacuum. Finally, the target compound was isolated by rapid column chromatography.

$^1$H NMR spectrum was measured by Bruker instrument (200-400 MHz), and chemical shift was expressed in ppm. Chloroform was used as a reference standard (7.25 ppm) or tetramethylsilane was used as an internal standard (0.00 ppm). Other solvents commonly used in NMR might also be used when necessary. $^1$H NMR was expressed as follows: s=singlet, d=doublet, t=triplet, m=multiplet, br=broadened, dd=doublet of doublets, and dt=doublet of triplets. If a coupling constant was provided, it was in the unit of Hz.

A mass spectrum was determined by LC/MS, and an ionization method may be ESI or APCI. All melting points were uncorrected.

The following examples were only used for illustrating a synthesis method of a specific compound invented. However, the synthesis method was not limited. Compounds not listed below might also be prepared by the same synthesis route and synthesis method as below, and might be prepared by selecting appropriate starting raw materials and adjusting common-sense reaction conditions slightly where necessary.

Synthesis

The target compound in general structural formula (I) might be synthesized by a method shown in a synthesis route_1. The substituted o-fluoronitrobenzene derivative V is aminated and reduced to obtain VII. The intermediate VII was cyclized with appropriate acid or aldehyde to obtain VIII. Corresponding alcohol or mercapto derivative IX obtained by demethylating the latter reacted with a fluorinated derivative, thus obtaining a key intermediate XI. The XI was reduced, diazotized and cyclized to obtain the target compound as shown in general structural formula (I).

Synthesis Route_1

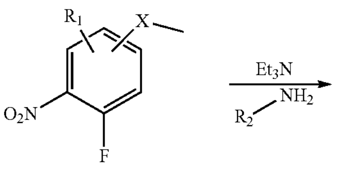

V

-continued

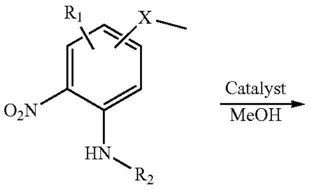

VI

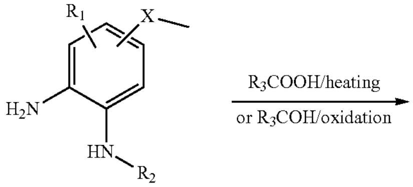

VII

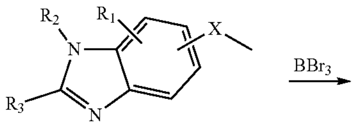

VIII

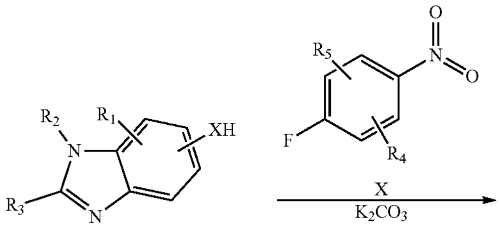

IX

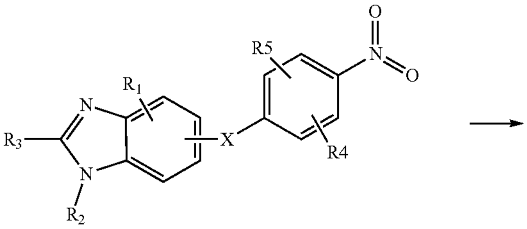

XI

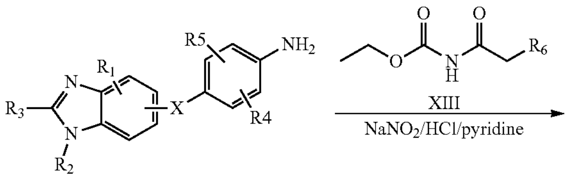

XII

-continued

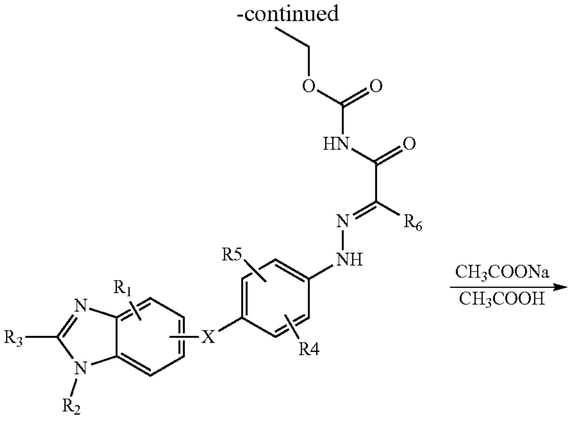

XIV

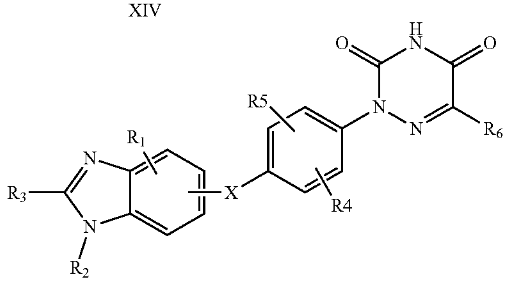

General formula (I)

In the general structural formula (I), when $R^1$ and $R^3$=H, and $R^2$=methyl, a corresponding target compound XXIII might be synthesized by a method shown in synthesis route_2.

Synthesis Route_2

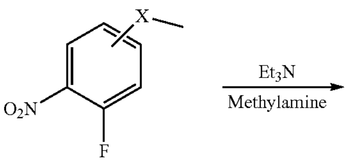

XV

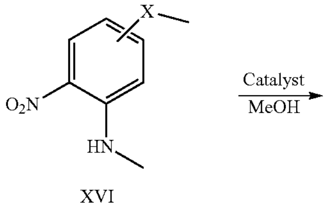

XVI

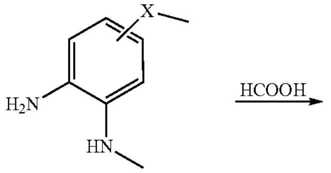

XVII

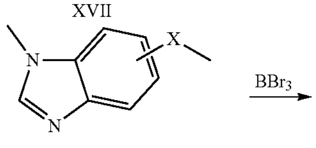

XVIII

-continued

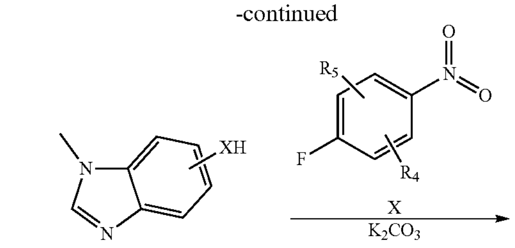

XIX

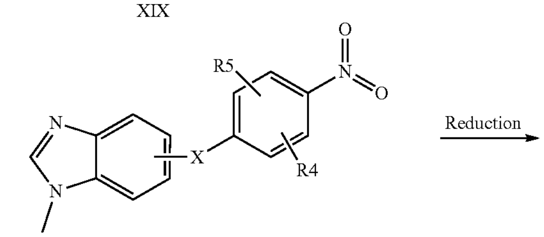

XX

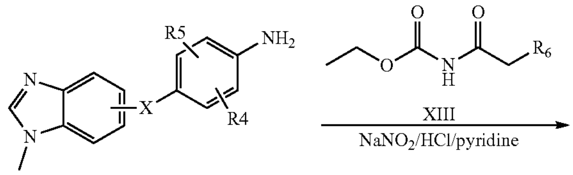

XXI

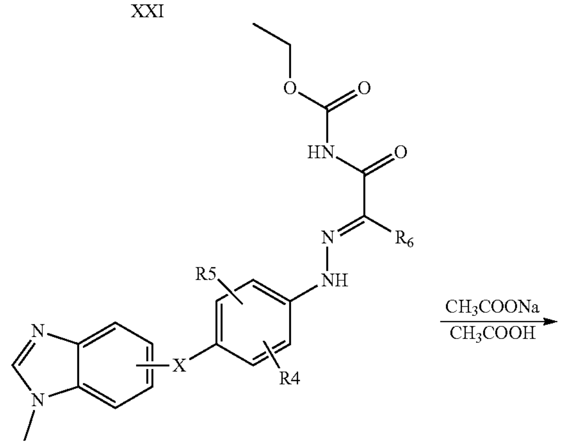

XXII

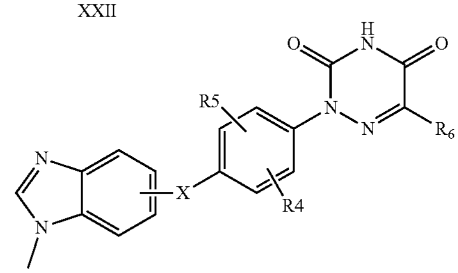

XXIII

Specifically, when $R^1$ and $R^3$=H, $R^2$=methyl, while X=O, S, the compound XXIII shown in structural general formula (I) might be prepared using an appropriate o-flouro-mitrobrnzene derivative XV as a raw material, under the action of triethylamine to obtain a compound XVI. Under the catalysis of an appropriate catalyst (such as palladium on carbon), XVII was obtained by reduction. Then, the intermediate XVII and formic acid were heated for a cyclization reaction to obtain XVIII. Under the action of boron tribromide, XVIII was demethylated to obtain a corresponding alcohol or mercapto derivative XIX. The latter was condensed under an alkaline condition with an appropriate compound X to form a corresponding XX. XX was reduced (for example, reduced by iron powder), diazotized, and then reacted with XIII to obtain XXII. Under the action of acetic acid-sodium acetate, the target compound XXIII was obtained by cyclization.

Synthesis Route_3

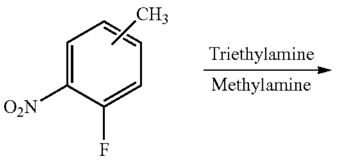

XVI

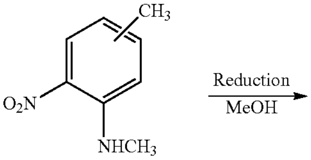

XVII

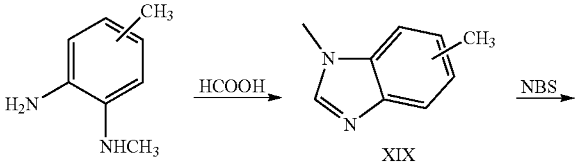

XVIII

XIX

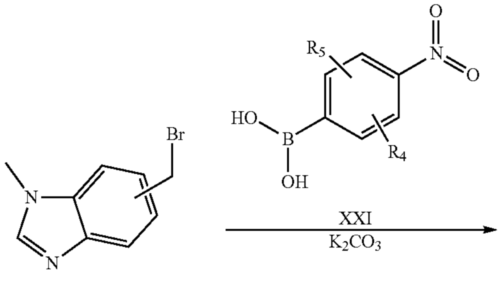

XX

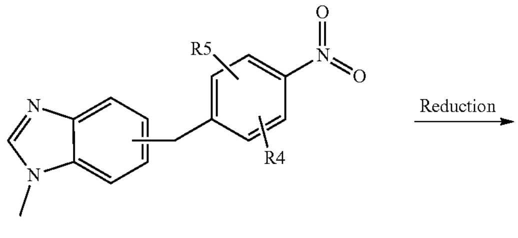

XXII

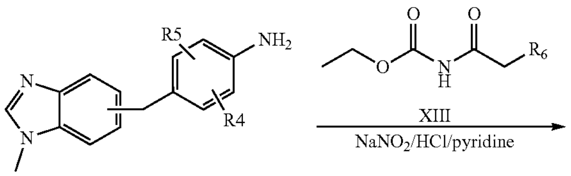

XXIII

-continued

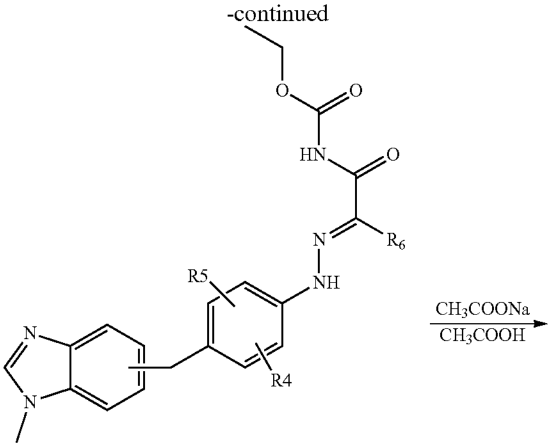

XXIV

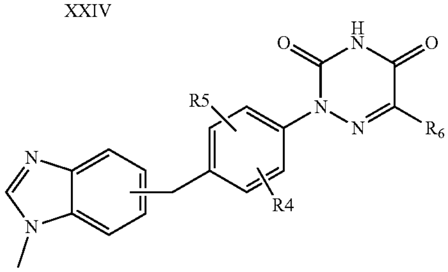

XXV

In general structural formula (I), when $R^1$ and $R^3$=H, $R^2$=methyl, while X=$CH_2$, a corresponding target compound XXV might be synthesized by a method shown in a synthesis route_3. Specifically, the compound shown in structural general formula (I) might be prepared using an appropriate o-fluoronitrobenzene derivative XVI as a raw material under the action of triethylamine to obtain a compound XVII. Under the catalysis of an appropriate catalyst (such as palladium on carbon), XVIII was obtained by reduction. Then, the intermediate XVIII and formic acid were heated for a cyclization reaction to obtain a corresponding XIX. Under the action of NBS, XIX was converted into a bromine-substituted derivative XX. The latter was condensed with an appropriate boronic acid derivative XXI to obtain XXII. XXII was reduced (for example, reduced by iron powder), diazotized, and then reacted with XIII to obtain XXIV. Under the action of acetic acid-sodium acetate, the target compound XXV was obtained by cyclization.

The contents of the present invention will be further described in detail below with reference to the examples. The purpose is to make technicians with basic knowledge in the art more clearly understand and practice the specific content of the present invention. However, the scope of protection of the present invention is not limited to these examples.

Example 1

Preparation of 2-(3,5-dibromo-4-((1-methyl-1H-benzo[d]imidazol-6-yl)oxy)phenyl)-3,5-dioxo-2,3,4,5-tetra hydro-1,2,4-triazine-6-carbonitrile (1)

The compound (compound 1) of Example 1 may be implemented by the method in the above-mentioned synthesis route_1. Specifically, as long as the required raw materials were selected, the compound may be synthesized by a specific route represented by the following formula.

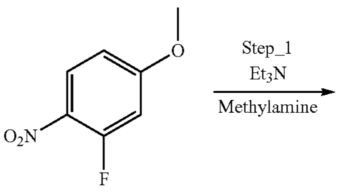

V-1

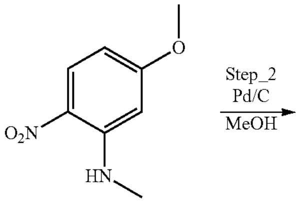

VI-1

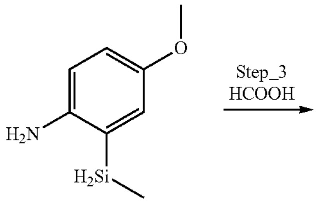

VII-1

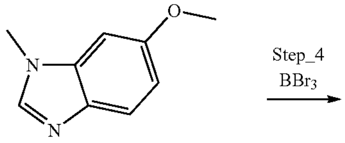

VIII-1

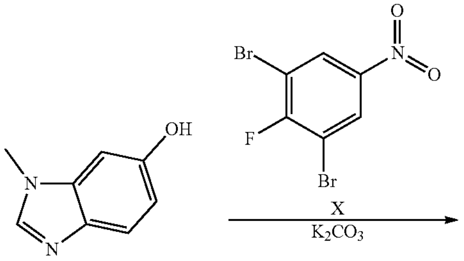

IX-1

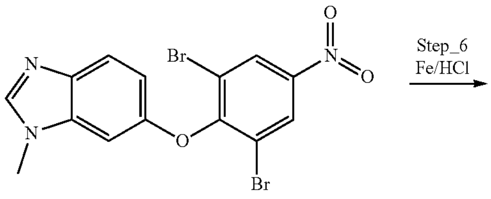

XI-1

Step_7

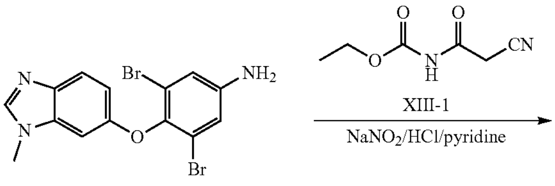

XII-1

-continued

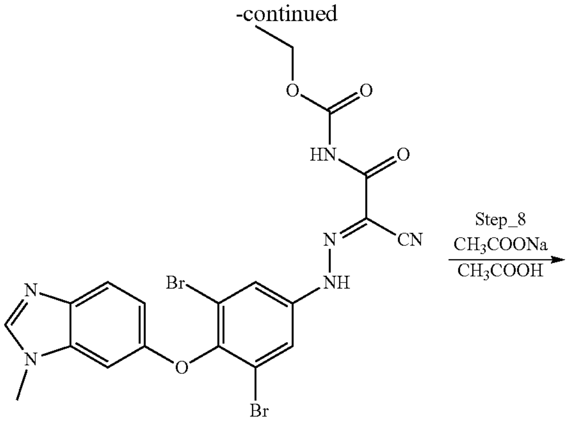

XIV-1

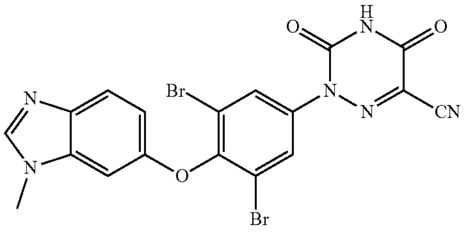

1
(XIV-1)

Step_1 Synthesis of 5-methoxy-N-methyl-2-nitroaniline (VI-1)

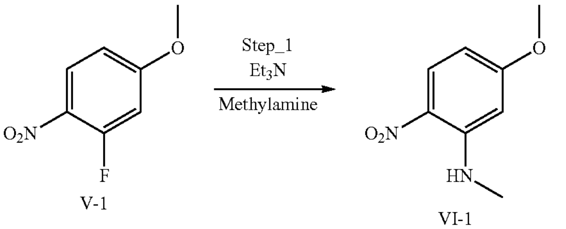

V-1

VI-1

In a sealed tube, V-1 (5.13 g, 30.0 mmol), tetrahydrofuran (5 mL), triethylamine (9.10 g, 90.0 mmol) and 2 M methylamine in furan (30 mL, 60 mmol) (40.0 g, 0.2 mol) were added sequentially. The reaction was heated overnight at 60° C. Then, the reaction was cooled to room temperature, the solvent was removed under reduced pressure. 100 mL of ethyl acetate was added and the system was washed with water twice (50 mL each time); washed with salt solution once (50 mL), and then dried with $Na_2SO_4$. After the solvent was removed under reduced pressure, the system was recrystallized with petroleum ether-ethyl acetate (petroleum ether/ethyl acetate, 1/1, 15 mL) to obtain the title compound VI-1 (white solid; 3.95 g; and yield: 72%). $^1H$ NMR (400 MHz, $CDCl_3$): δ8.28 (br s, 1H), 8.13 (d, J=9.2 Hz, 1H), 6.23 (dd, J=9.6, 2.4 Hz, 1H), 6.12 (d, J=2.4 Hz, 1H), 3.88 (m, 3H), 3.00 (d, J=5.2 Hz, 3H).

Step_2 Synthesis of 5-methoxy-N[1]-methylbenzene-1,2-diamine (VII-1)

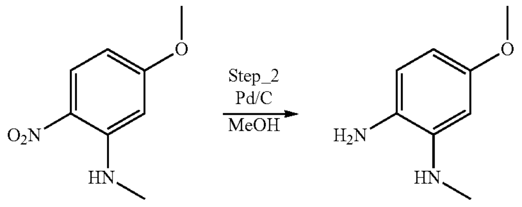

VI-1 VII-1

Pd/C (10%, 800 mg) was added to methanol solution (50 mL) containing VI-1 (3.95 g, 21.7 mmol). The reaction was introduced with hydrogen (1 atm) under stirring and heated at 50° C. for 6 hours. The reactants were cooled to room temperature, filtered and then concentrated to obtain VII-1 (brown solid; 3.25 g; and yield: 98%). $^1$H NMR (400 MHz, $CDCl_3$): δ6.34 (d, J=8.0 Hz, 1H), 6.25 (d, J=2.4 Hz, 1H), 6.18 (dd, J=8.4, 2.8 Hz, 1H), 3.76 (s, 3H), 2.84 (s, 3H).

Step_3 Synthesis of 6-methoxy-1-methyl-1H-benzo[d]imidazole (VIII-1)

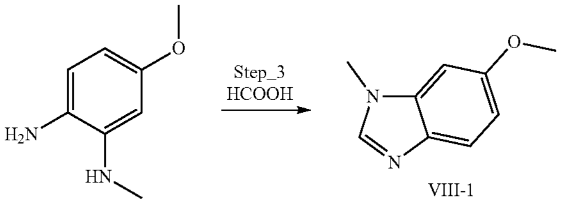

VII-1 VIII-1

VII-1 (3.25 g, 21.4 mmol) was dissolved in formic acid solution (20 mL) and heated to 50° C. overnight. The reaction was cooled and concentrated under reduced pressure. The reaction was neutralized with excess saturated sodium bicarbonate solution and stirred for 10 minutes. The reaction was washed twice with dichloromethane-methanol (20/1, 200 mL). The washing solutions were combined, then washed with oxygen-saturated salt solution, dried with $Na_2SO_4$ and filtered. The filtrate was concentrated to obtain an oily substance, namely the title compound VIII-1 (3.4 g, yield: 94%). $^1$H NMR (400 MHz, $CDCl_3$): δ7.75 (s, 1H), 7.67 (d, J=8.8 Hz, 1H), 6.62 (dd, J=8.4, 2.4 Hz, 1H), 6.82 (d, J=2.8 Hz, 1H), 3.88 (s, 3H), 3.78 (s, 3H).

Step_4 Synthesis of 1-methyl-1H-benzo[d]imidazol-6-ol (IX-1)

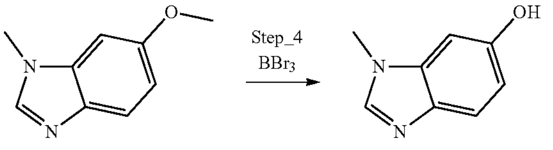

VIII-1 IX-1

With nitrogen at −78° C., VIII-1 (3.24 g, 20.0 mmol) was added into a reaction flask filled with dichloromethane solution of boron tribromide (1 M, 80 mL, 80 mmol). Then, the system was naturally heated to room temperature, and reacted overnight under stirring. The system was concentrated and was neutralized with saturated sodium bicarbonate solution till that pH=8. The system was washed three times with dichloromethane-methanol solution (10/1, 200 mL). The extract was washed with water and then dried with $Na_2SO_4$. The obtained product was filtered and concentrated to obtain the title compound IX-1 (brown solid, 2.0 g, yield: 68%). $^1$H NMR (400 MHz, $CDCl_3$): δ9.29 (s, 1H), 7.94 (s, 1H), 7.41 (d, J=8.4 Hz, 1H), 6.82 (d, J=2.0 Hz, 1H), 6.71 (q, J=2.4 Hz, 1H), 3.72 (s, 3H).

Step_5 Synthesis of 6-(2,6-dibromo-4-nitrophenoxy)-1-methyl-1H-benzo[d]imidazole (XI-1)

Step_5

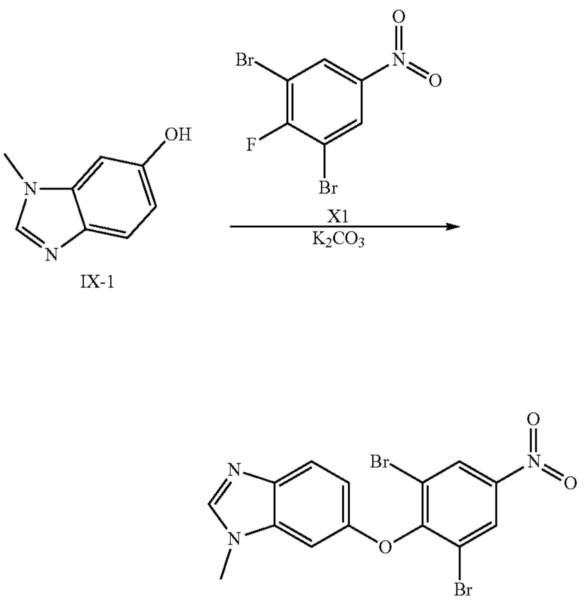

IX-1

XI-1

In a reaction flask, IX-1 (430 mg, 2.90 mmol), dimethylsulfoxide (10 mL), sodium carbonate (802 mg, 5.81 mmol) and X-1 (890 mg, 3.0 mmol) were added sequentially. The reactants were stirred for 2 hours at 50° C. After the reactants were cooled to room temperature, ethyl acetate was added (100 mL). The organic phase was washed with water three times, with 30 mL each time. Then the reaction was washed with saturated salt solution (30 mL), and dried with $Na_2SO_4$, and filtered. The filtrate was concentrated and crystallized in petroleum ether-ethyl acetate (1/1, 15 mL) to obtain the title compound XI-1 (white solid, 1.1 g, yield: 89%). $^1$H NMR (400 MHz, DMSO-$d_6$): δ8.66 (s, 2H), 8.13 (s, 1H), 7.61 (d, J=9.2 Hz, 1H), 7.05 (d, J=2.4 Hz, 1H), 6.80 (dd, J=9.2, 2.8 Hz, 1H), 3.75 (s, 3H).

Step_6 Synthesis of 3,5-dibromo-4-((methyl-1H-benzo[d]imidazol-6-yl)oxy)aniline (XII-1)

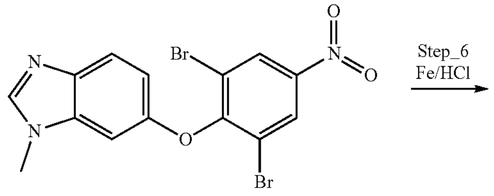

XI-1

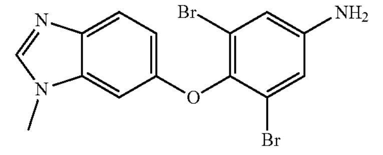

XII-1

Step_7 Synthesis of (E)-ethyl-(2-cyano-2-(2-(3,5-dibromo-4-((1-methyl-1H-benzo[d]imidazol-6-yl)oxy)phenyl) hydrazineylidene)acetyl) carbamate (XIV-1)

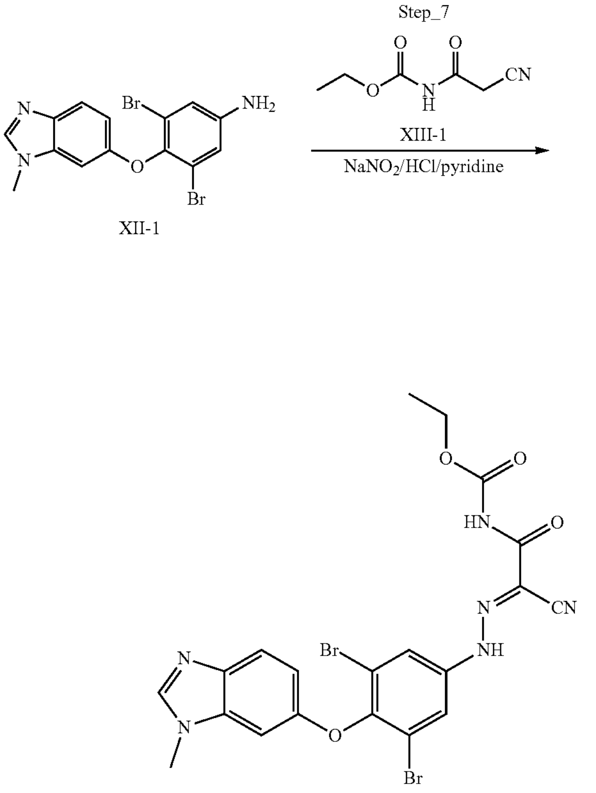

XII-1

XIV-1

XI-1 (1.00 g, 2.34 mmol), ethanol (50 mL) and iron powder (1.31 g, 23.4 mmol) were added into a reaction flask sequentially, and heated to 75° C. under stirring. Then concentrated hydrochloric acid (2 mL) was added dropwise. The reaction was continued at 75° C. for 30 minutes. Then the reaction was cooled to room temperature and filtered. The system was concentrated and neutralized with saturated aqueous solution of sodium carbonate (50 mL). The system was extracted three times with dichloromethane-methanol solution (10/1, 150 mL). The extract was washed with water and then dried with $Na_2SO_4$. The dried extract was filtered and concentrated to obtain the title compound XII-1 (white solid, 830 mg, yield: 89%). $^1H$ NMR (400 MHz, $CDCl_3$): δ8.08 (s, 1H), 7.55 (d, J=8.4 Hz, 1H), 6.92 (s, 2H), 6.86 (d, J=2.8 Hz, 1H), 6.69 (dd, J=8.8, 2.4 Hz, 1H), 5.61 (br s, 2H), 3.73 (s, 3H).

Concentrated hydrochloric acid (0.15 mL) was added to an aqueous solution (7.5 mL) containing XII-1 (300 mg, 0.76 mmol). The mixture was stirred at room temperature to obtain a clear solution. The reaction was cooled to 0° C. Water (1.2 mL) solution containing $NaNO_2$ (62 mg, 0.76 mmol) was added dropwise with stirring, and a temperature of the reaction suspension was kept at 5° C. or lower. After the dropwise addition was completed, the reaction was continuously stirred at 0° C. for 1 hour. The reaction liquid was added dropwise to a pyridine-water solution (8 mL-3.6 mL) containing XIII-1 (142 mg, 0.910 mmol), and the reaction temperature was kept at 5° C. or lower. The resulting reaction solution was continuously stirred at 5° C. for 1 hour. The reaction solution was poured into saturated sodium bicarbonate solution (20 mL) and extracted three times with dichloromethane-methanol solution (10/1, 100 mL). The extract was washed with water and then dried with $Na_2SO_4$. The dried extract was filtered and concentrated, then was separated by C18 column separation (development system: 5-95% $CH_3CN$ aqueous solution, 25 minutes) to obtain the title compound XIV-1 (white solid, 240 mg, yield: 56%). $^1H$ NMR (400 MHz, DMSO-$d_6$): δ10.76 (s, 1H), 8.18 (s, 1H), 8.16 (s, 2H), 7.60 (d, J=8.8 Hz, 1H), 6.95 (d, J=2.4 Hz, 1H), 6.76 (dd, J=8.8, 2.8 Hz, 1H), 4.19 (q, J=6.8 Hz, 2H), 3.75 (s, 3H), 1.27 (t, J=6.8 Hz, 3H).

Step_8 Preparation of 2-(3,5-dibromo-4-((1-methyl-1H-benzo[d]imidazol-6-yl)oxy)phenyl)-3,5-dioxo-2,3,4,5-tetra hydro-1,2,4-triazine-6-carbonitrile (XV-1)

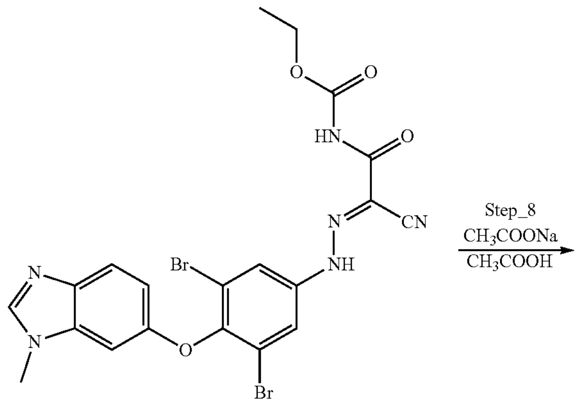

XIV-1

-continued

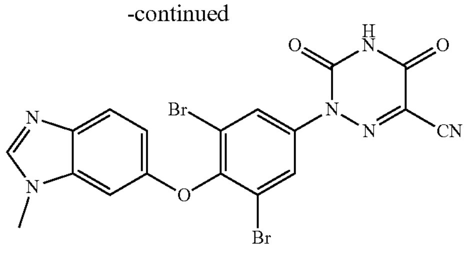

1
(XIV-1)

Sodium acetate (179 mg, 2.19 mmol) was added to a suspension of acetic acid (10 mL) containing XIV-1 (310 mg, 0.550 mmol). The obtained reaction solution was stirred at 120° C. for 2 hours. The reactants were cooled to room temperature and concentrated. The system was separated by C18 column separation (development system: 5-95% $CH_3CN$ aqueous solution, 25 minutes) to obtain the title compound XIV-1 (white solid, 100 mg, yield: 35%). $^1H$ NMR (400 MHz, DMSO-$d_6$): δ8.16 (s, 1H), 7.97 (s, 2H), 7.61 (d, J=8.8 Hz, 1H), 7.05 (d, J=2.4 Hz, 1H), 6.75 (dd, J=8.8, 2.4 Hz, 1H), 3.77 (s, 3H). LC-MS [mobile phase: within 6.5 minutes, from 80% water (0.02% $NH_4OAc$) and 20% $CH_3CN$ to 30% water (0.02% $NH_4OAc$) and 70% $CH_3CN$], Rt=2.732 minutes; purity: 96.19% (254 nm), MS calculated value: 515.9; and MS actually measured value: 516.9 $[M+H]^+$.

Examples 2 to 12

According to the method of Example 1, various derivatives can be synthesized by appropriately changing the starting materials. Examples 2-12 are some representative examples (see Table 1).

TABLE 1

| Example | Structure | Name | m/z$[MH]^+$ |
|---|---|---|---|
| 2 | 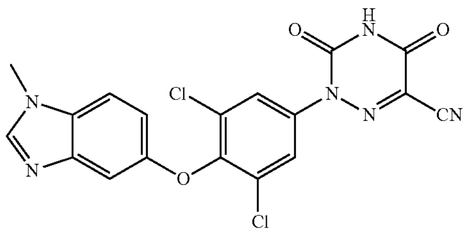 2 | 2-(3,5-dichloro-4-((1-methyl-1H-benzo[d]imidazol-5-yl)oxy)phenyl)-3,5-dioxo-2,3,4,5-tetrahydro-1,2,4-triazine-6-carbonitrile | 429.22 |
| 3 | 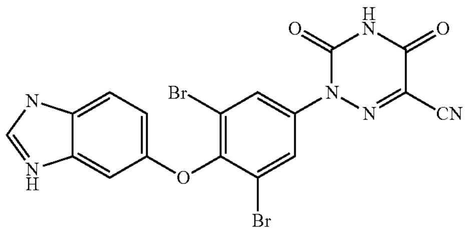 3 | 2-(4-((1H-benzo[d]imidazol-6-yl)oxy)-3,5-dibromophenyl)-3,5-dioxo-2,3,4,5-tetrahydro-1,2,4-triazine-6-carbonitrile | 501.90 |

TABLE 1-continued

| Example | Structure | Name | m/z[MH]+ |
|---|---|---|---|
| 4 | 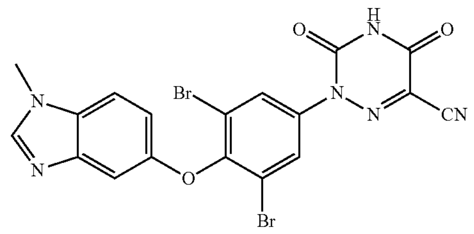 4 | 2-(3,5-dibromo-4-((1-methyl-1H-benzo[d]imidazol-5-yl)oxy)phenyl)-3,5-dioxo-2,3,4,5-tetrahydro-1,2,4-triazine-6-carbonitrile | 515.92 |
| 5 | 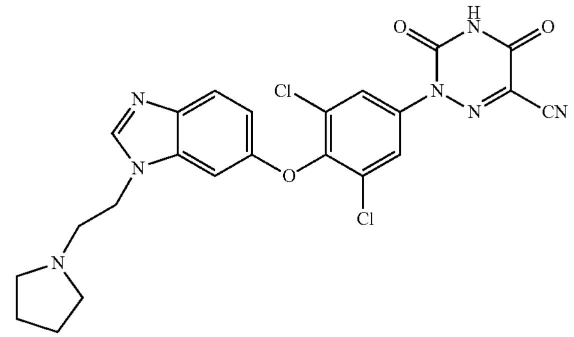 5 | 2-(3,5-dichloro-4-((1-(2-pyrrolidin-1-yl)ethyl)-1H-benzo[d]imidazol-6-yl)oxy)phenyl)-3,5-dioxo-2,3,4,5-tetrahydro-1,2,4-triazine-6-carbonitrile | 512.35 |
| 6 | 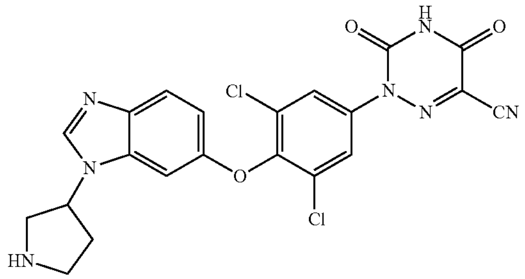 6 | 2-(3,5-dichloro-4-((1-pyrrolidin-3-yl)-1H-benzo[d]imidazol-6-yl)oxy)phenyl)-3,5-dioxo-2,3,4,5-tetrahydro-1,2,4-triazine-6-carbonitrile | 483.06 |
| 7 | 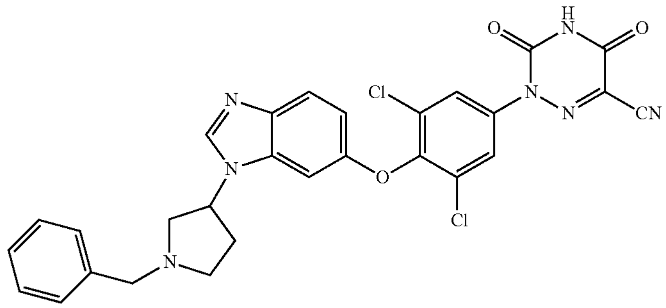 7 | 2-(4-((1-(1-benzylpyrrolidin-3-yl)-1H-benzo[d]imidazol-6-yl)oxy)-3,5-dichlorophenyl)-3,5-dioxo-2,3,4,5-tetrahydro-1,2,4-triazine-6-carbonitrile | 574.42 |

TABLE 1-continued

| Example | Structure | Name | m/z[MH]+ |
|---|---|---|---|
| 8 | 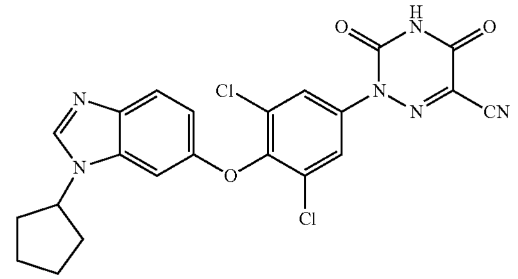 8 | 2-(3,5-dichloro-4-((1-cyclopentyl-1H-benzo[d]imidazol-6-yl)oxy)phenyl)-3,5-dioxo-2,3,4,5-tetrahydro-1,2,4-triazine-6-carbonitrile | 482.07 |
| 9 | 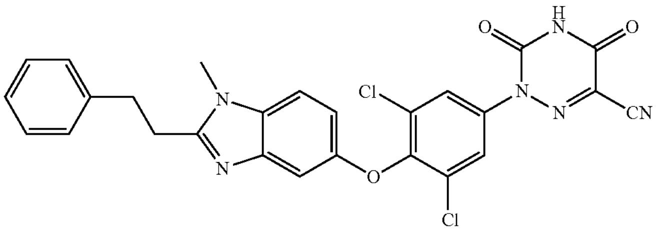 9 | 2-(3,5-dichloro-4-((1-methyl-2-phenethyl-1H-benzo[d]imidazol-5-yl)oxy)phenyl)-3,5-dioxo-2,3,4,5-tetrahydro-1,2,4-triazine-6-carbonitrile | 532.08 |
| 10 | 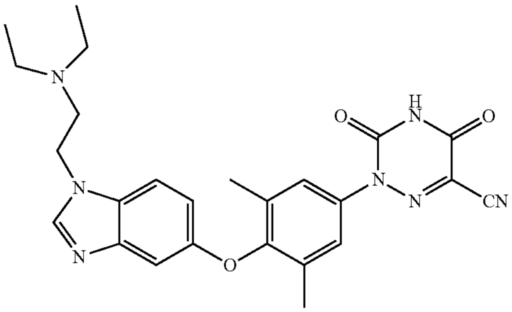 10 | 2-(4-((1-(2-diethylamino)ethyl)-1H-benzo[d]imidazol-5-yl)oxy)-3,5-dimethylphenyl)-3,5-dioxo-2,3,4,5-tetrahydro-1,2,4-triazine-6-carbonitrile | 473.22 |
| 11 | 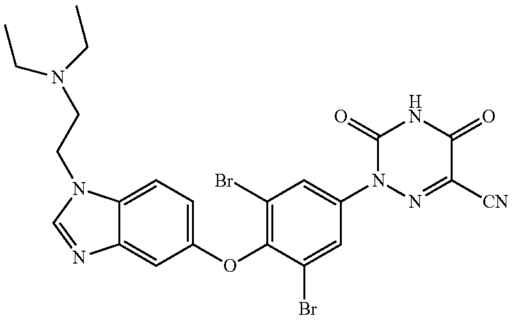 11 | 2-(3,5-dibromo-4-((1-(2-(diethylamino)ethyl)-1H-benzo[d]imidazol-5-yl)oxy)phenyl)-3,5-dioxo-2,3,4,5-tetrahydro-1,2,4-triazine-6-carbonitrile | 601.01 |
| 12 | 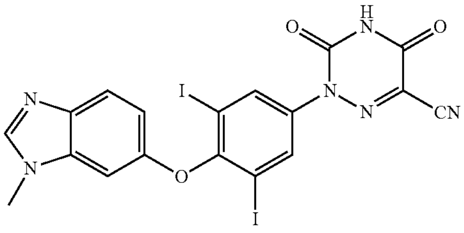 12 | 2-(3,5-diiodo-4-((1-methyl-1H-benzo[d]imidazol-6-yl)oxy)phenyl)-3,5-dioxo-2,3,4,5-tetrahydro-1,2,4-triazine-6-carbonitrile | 611.89 |

TABLE 1-continued

| Example | Structure | Name | m/z[MH]+ |
|---|---|---|---|
| 13 | 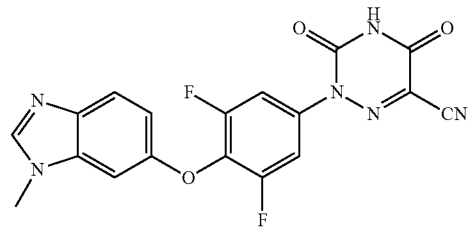 13 | 2-(3,5-difluoro-4-((1-methyl-1H-benzo[d]imidazol-6-yl)oxy)phenyl)-3,5-dioxo-2,3,4,5-tetrahydro-1,2,4-triazine-6-carbonitrile | 396.08 |
| 14 | 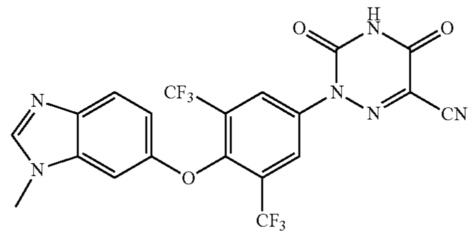 14 | 2-(4-((1-methyl-1H-benzo[d]imidazol-6-yl)oxy)-3,5-bis(trifluoromethyl)phenyl)-3,5-dioxo-2,3,4,5-tetrahydro-1,2,4-triazine-6-carbonitrile | 496.07 |
| 15 | 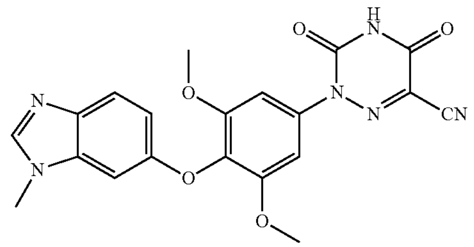 15 | 2-(3,5-dimethoxy-4-((1-methyl-1H-benzo[d]imidazol-6-yl)oxy)phenyl)-3,5-dioxo-2,3,4,5-tetrahydro-1,2,4-triazine-6-carbonitrile | 420.12 |
| 16 | 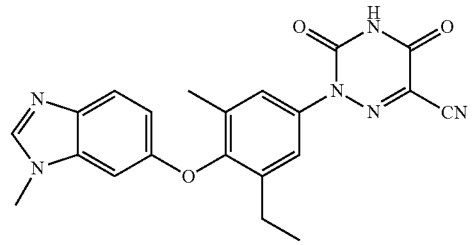 16 | 2-(3-ethyl-5-methyl-4-((1-methyl-1H-benzo[d]imidazol-6-yl)oxy)phenyl)-3,5-dioxo-2,3,4,5-tetrahydro-1,2,4-triazine-6-carbonitrile | 402.14 |
| 17 | 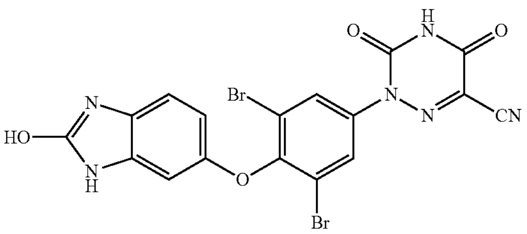 17 | 2-(3,5-dibromo-4-((2-hydroxy-1H-benzo[d]imidazol-6-yl)oxy)phenyl)-3,5-dioxo-2,3,4,5-tetrahydro-1,2,4-triazine-6-carbonitrile | 517.90 |

TABLE 1-continued

| Example | Structure | Name | m/z[MH]+ |
|---|---|---|---|
| 18 | 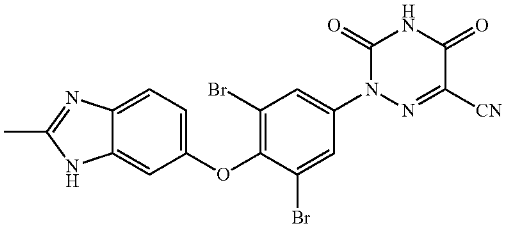 18 | 2-(3,5-dibromo-4-((2-methyl-1H-benzo[d]imidazol-6-yl)oxy)phenyl)-3,5-dioxo-2,3,4,5-tetrahydro-1,2,4-triazine-6-carbonitrile | 515.92 |
| 19 | 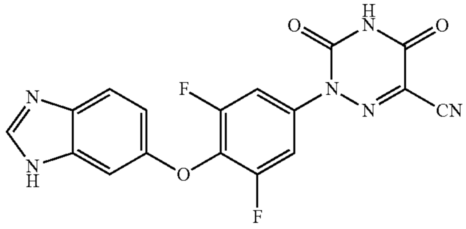 19 | 2-(4-((1H-benzo[d]imidazol-6-yl)oxy)-3,5-difluorophenyl)-3,5-dioxo-2,3,4,5-tetrahydro-1,2,4-triazine-6-carbonitrile | 382.06 |
| 20 | 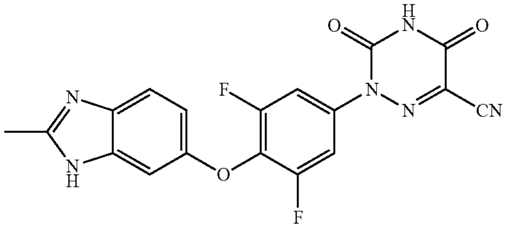 20 | 2-(3,5-difluoro-4-((2-methyl-1H-benzo[d]imidazol-6-yl)oxy)phenyl)-3,5-dioxo-2,3,4,5-tetrahydro-1,2,4-triazine-6-carbonitrile | 396.08 |
| 21 | 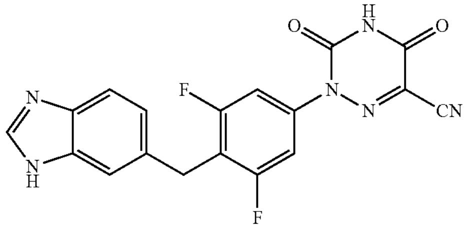 21 | 2-(4-((1H-benzo[d]imidazol-6-yl)methyl)-3,5-difluorophenyl)-3,5-dioxo-2,3,4,5-tetrahydro-1,2,4-triazine-6-carbonitrile | 380.08 |
| 22 | 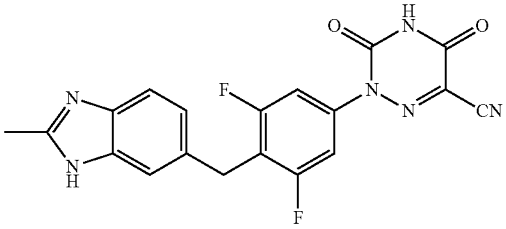 22 | 2-(3,5-difluoro-4-((2-methyl-1H-benzo[d]imidazol-6-yl)methyl)phenyl)-3,5-dioxo-2,3,4,5-tetrahydro-1,2,4-triazine-6-carbonitrile | 394.10 |

TABLE 1-continued

| Example | Structure | Name | m/z[MH]$^+$ |
|---|---|---|---|
| 23 | 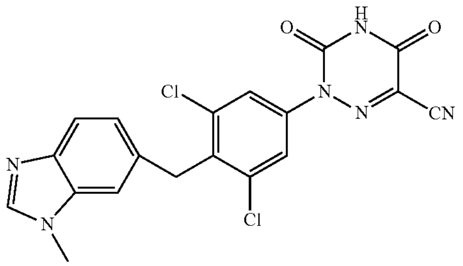 23 | 2-(3,5-dichloro-4-((1-methyl-1H-benzo[d]imidazol-6-yl)methyl) phenyl)-3,5-dioxo-2,3,4,5-tetrahydro-1,2,4-triazine-6-carbonitril | 426.04 |
| 24 | 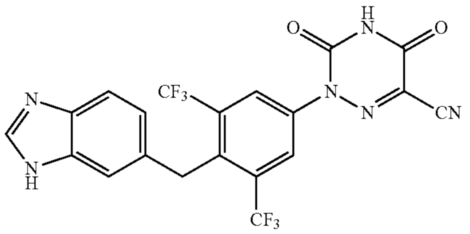 24 | 2-(4-((1H-benzo[d]imidazol-6-yl)methyl)-3,5-bis(trifluoro-methyl)phenyl)-3,5-dioxo-2,3,4,5-tetrahydro-1,2,4-triazine-6-carbonitrile | 480.08 |

Furthermore, synthesis route_1 or synthesis route_2 may be selected, with reference to the method in Example 1, wider range of various derivatives can be synthesized by appropriately selecting the starting materials. The compounds listed in Table 2 are some of the examples.

TABLE 2

25

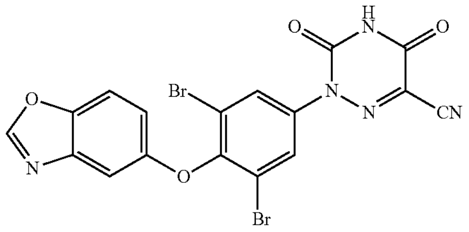 [SMILES: N#Cc1nn(-c2cc(Br)c(Oc3ccc4ocnc4c3)c(Br)c2)c(=O)[nH]c1=O]

m/z[MH]$^+$ 502.89

26

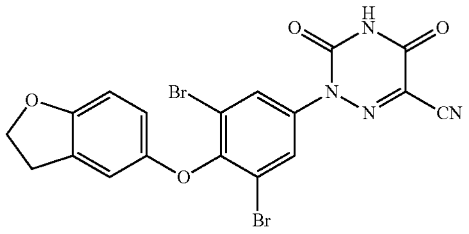 [SMILES: N#Cc1nn(-c2cc(Br)c(Oc3ccc4c(c3)CCO4)c(Br)c2)c(=O)[nH]c1=O]

m/z[MH]$^+$ 503.91

TABLE 2-continued

27

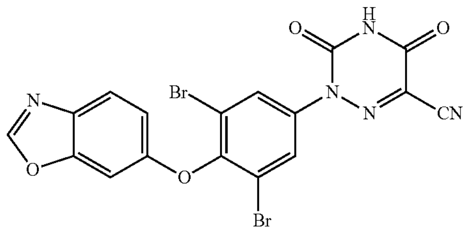 [SMILES: N#Cc1nn(-c2cc(Br)c(Oc3ccc4ncoc4c3)c(Br)c2)c(=O)[nH]c1=O]

m/z[MH]$^+$ 502.89

28

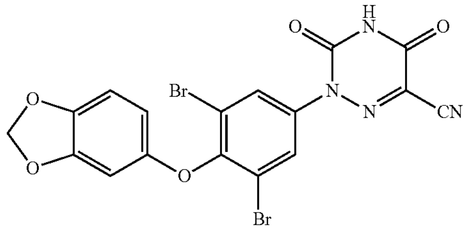 [SMILES: N#Cc1nn(-c2cc(Br)c(Oc3ccc4c(c3)OCO4)c(Br)c2)c(=O)[nH]c1=O]

m/z[MH]$^+$ 505.89

29

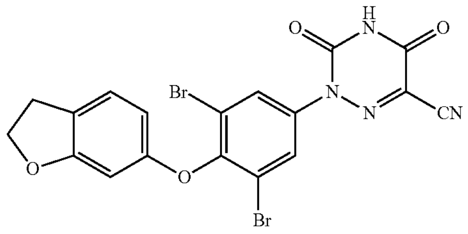

m/z[MH]$^+$ 503.91

TABLE 2-continued
30
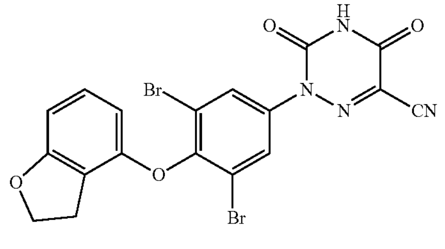 [SMILES: N#Cc1nn(-c2cc(Br)c(Oc3cccc4c3CCO4)c(Br)c2)c(=O)[nH]c1=O]
m/z[MH]+ 503.91
31
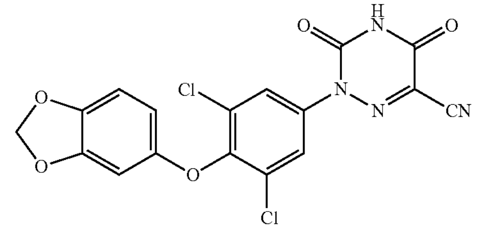 [SMILES: N#Cc1nn(-c2cc(Cl)c(Oc3ccc4c(c3)OCO4)c(Cl)c2)c(=O)[nH]c1=O]
m/z[MH]+ 417.99
32
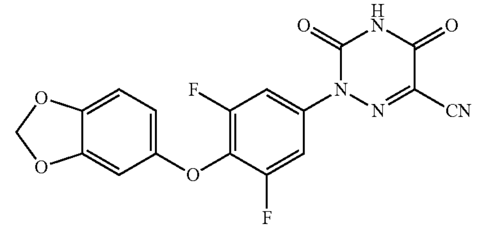 [SMILES: N#Cc1nn(-c2cc(F)c(Oc3ccc4c(c3)OCO4)c(F)c2)c(=O)[nH]c1=O]
m/z[MH]+ 386.05
33
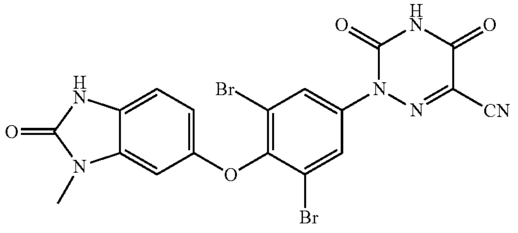 [SMILES: Cn1c(=O)[nH]c2ccc(Oc3c(Br)cc(-n4nc(C#N)c(=O)[nH]c4=O)cc3Br)cc21]
m/z[MH]+ 531.91
34
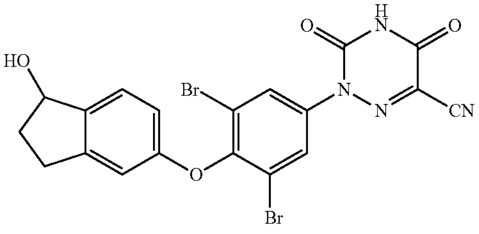 [SMILES: N#Cc1nn(-c2cc(Br)c(Oc3ccc4c(c3)CCC4O)c(Br)c2)c(=O)[nH]c1=O]
m/z[MH]+ 517.92
TABLE 2-continued
35
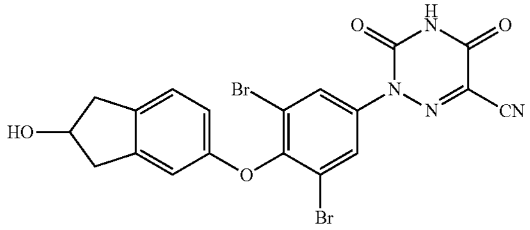 [SMILES: N#Cc1nn(-c2cc(Br)c(Oc3ccc4c(c3)CC(O)C4)c(Br)c2)c(=O)[nH]c1=O]
m/z[MH]+ 517.92
36
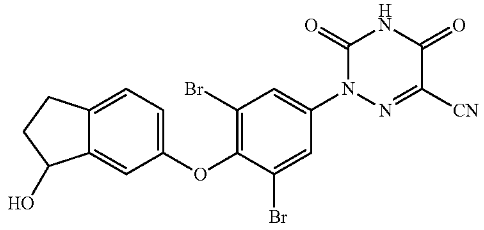 [SMILES: N#Cc1nn(-c2cc(Br)c(Oc3ccc4c(c3)C(O)CC4)c(Br)c2)c(=O)[nH]c1=O]
m/z[MH]+ 517.92
37
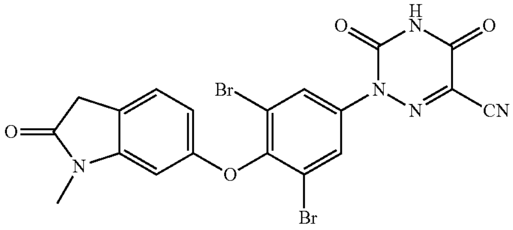 [SMILES: CN1C(=O)Cc2ccc(Oc3c(Br)cc(-n4nc(C#N)c(=O)[nH]c4=O)cc3Br)cc21]
m/z[MH]+ 530.92
38
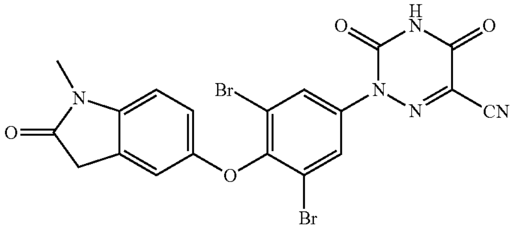 [SMILES: CN1C(=O)Cc2cc(Oc3c(Br)cc(-n4nc(C#N)c(=O)[nH]c4=O)cc3Br)ccc21]
m/z[MH]+ 530.92
39
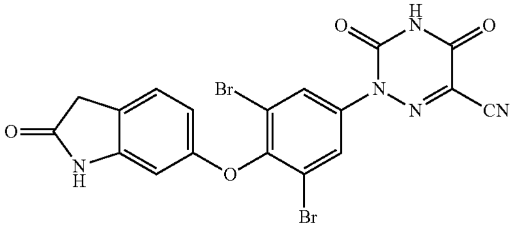 [SMILES: N#Cc1nn(-c2cc(Br)c(Oc3ccc4c(c3)NC(=O)C4)c(Br)c2)c(=O)[nH]c1=O]
m/z[MH]+ 516.90

TABLE 2-continued
40
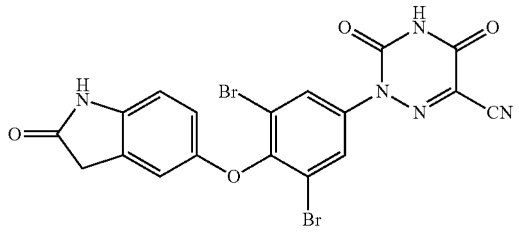 [SMILES: N#Cc1nn(-c2cc(Br)c(Oc3ccc4c(c3)CC(=O)N4)c(Br)c2)c(=O)[nH]c1=O]
m/z[MH]+ 516.90
41
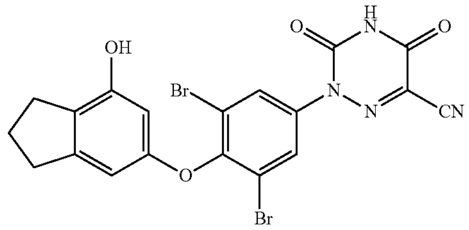 [SMILES: N#Cc1nn(-c2cc(Br)c(Oc3cc(O)c4c(c3)CCC4)c(Br)c2)c(=O)[nH]c1=O]
m/z[MH]+ 517.92
42
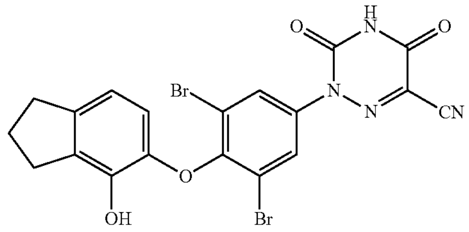 [SMILES: N#Cc1nn(-c2cc(Br)c(Oc3ccc4c(c3O)CCC4)c(Br)c2)c(=O)[nH]c1=O]
m/z[MH]+ 517.92
43
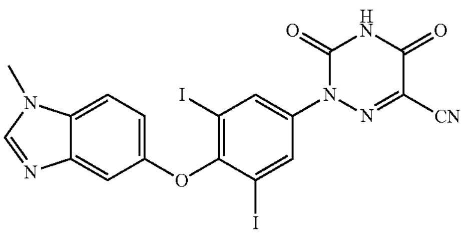 [SMILES: Cn1cnc2cc(Oc3c(I)cc(-n4nc(C#N)c(=O)[nH]c4=O)cc3I)ccc21]
m/z[MH]+ 611.89
44
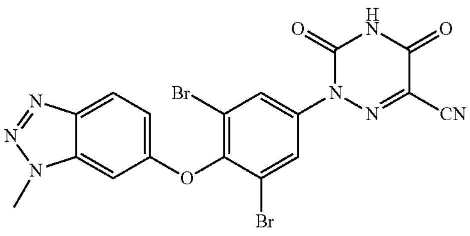 [SMILES: Cn1nnc2ccc(Oc3c(Br)cc(-n4nc(C#N)c(=O)[nH]c4=O)cc3Br)cc21]
m/z[MH]+ 516.91
TABLE 2-continued
45
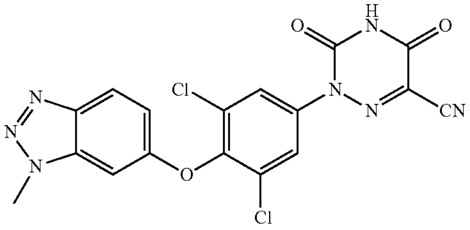 [SMILES: Cn1nnc2ccc(Oc3c(Cl)cc(-n4nc(C#N)c(=O)[nH]c4=O)cc3Cl)cc21]
m/z[MH]+ 429.01
46
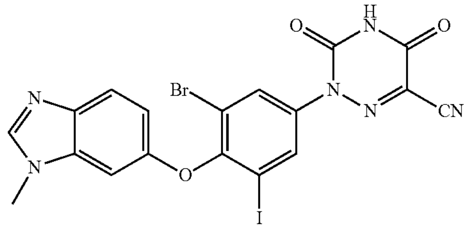 [SMILES: Cn1cnc2ccc(Oc3c(Br)cc(-n4nc(C#N)c(=O)[nH]c4=O)cc3I)cc21]
m/z[MH]+ 563.90
47
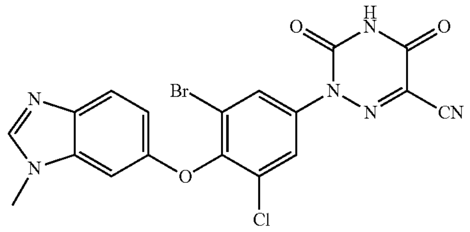 [SMILES: Cn1cnc2ccc(Oc3c(Cl)cc(-n4nc(C#N)c(=O)[nH]c4=O)cc3Br)cc21]
m/z[MH]+ 471.97
48
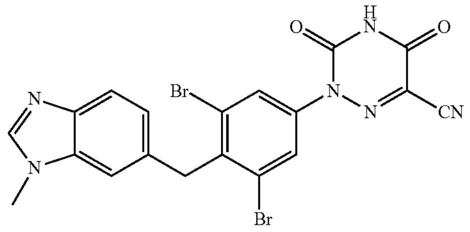 [SMILES: Cn1cnc2ccc(Cc3c(Br)cc(-n4nc(C#N)c(=O)[nH]c4=O)cc3Br)cc21]
m/z[MH]+ 513.94
49
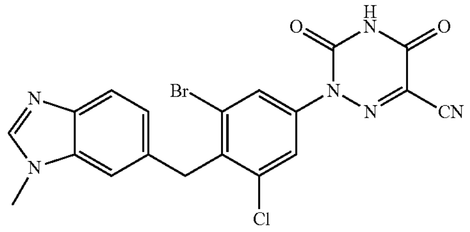
m/z[MH]+ 469.99

TABLE 2-continued

50

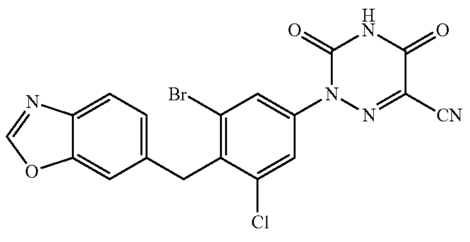 [SMILES: N#Cc1nn(-c2cc(Cl)c(Cc3ccc4ncoc4c3)c(Br)c2)c(=O)[nH]c1=O]

m/z[MH]+ 458.96

51

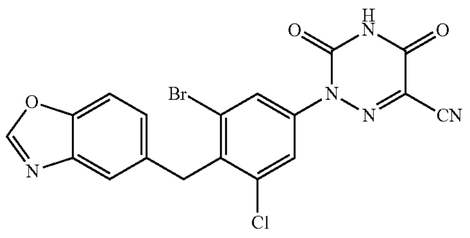 [SMILES: N#Cc1nn(-c2cc(Cl)c(Cc3ccc4ocnc4c3)c(Br)c2)c(=O)[nH]c1=O]

m/z[MH]+ 456.96

52

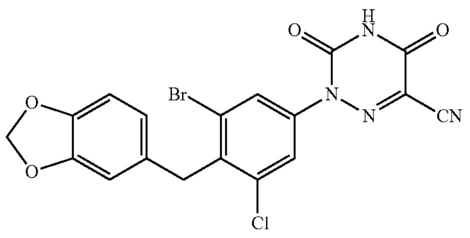

m/z[MH]+ 459.96

53

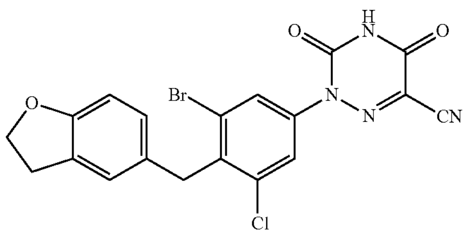 [SMILES: N#Cc1nn(-c2cc(Cl)c(Cc3ccc4c(c3)CCO4)c(Br)c2)c(=O)[nH]c1=O]

m/z[MH]+ 457.98

54

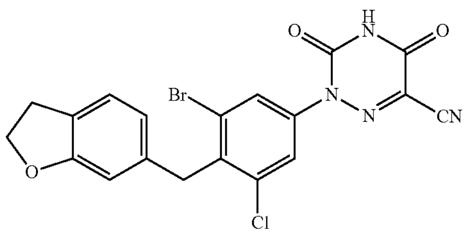 [SMILES: N#Cc1nn(-c2cc(Cl)c(Cc3ccc4c(c3)OCC4)c(Br)c2)c(=O)[nH]c1=O]

m/z[MH]+ 457.98

Pharmacological Test

I. THR-α/β activation effects of test compounds (compounds 1, 2, 4, 5, 6, 7, 8 and 9 in examples) were measured by the following methods.

Test Method 1

THR/RXR/GRIP1 Detection

Gene clones expressing a ligand-binding domain (amino acids 148-410) of THR-β (H6-THR-β) and a ligand-binding domain (amino acids 202-461) of THR-α (H6-THR-α) were inserted into an *Escherichia coli* expression vector pET28a, and the expression vector contained one N-terminal 6-His sequence. The expression vector was introduced into an *Escherichia coli* BL21 (DE3) strain to produce a recombinant protein with a His tag. The strain was inoculated into a TB culture medium (with a culture medium formula of: 3.3% trypsin, 2.5% yeast extract and 0.5% NaCl), added with IPTG with a final concentration of 0.2 mM, and cultured in a shaking flask at 25° C. for 24 hours. After finishing culturing, a bacterium in culture was collected, and the collected bacterium was resuspended with a lysis solution (0.05 M Tris, 0.3 M NaCl, 1% W/V betaine, 0.01 M imidazole, 0.02 M β-mercaptoethanol, and pH 8.0) with a volume 5 times that of the bacterium, and lysozyme and protease inhibitors were added at the same time, the treated bacteria was subjected to ultrasonic lysis (5 times per minute) in ice bath (4° C.). A lysed suspension was centrifuged at 127300 RCF for 2 hours, a supernatant was loaded on a NI_NTA agarose (Quigen 30210) column, and after washing with a buffer A, an H6-TRβ or H6-TRα protein was eluted with the buffer A containing 0.25 M imidazole.

A human retinol X receptor (amino acid 225-462) (RxRα) was subjected to engineering modification, so that an N-terminal of the human retinol X receptor had His6 and EE(EFMPME) tags, and then the human retinol X receptor was cloned into a pACYC vector, and produced a His6 EEtagged protein in *Escherichia coli*. IPTG with a final concentration of 0.1 mM was added into the culture medium for induction, and cultured in a shaking flask at 18° C. for 18 hours. After finishing culturing, a bacterium in culture was collected, and the collected bacterium was re-suspended with a lysis solution (0.05 M Tris, 0.3 M NaCl, 1% W/V betaine, 0.01 M imidazole, 0.02 β-mercaptoethanol, and pH 8.0) with a volume 5 times that of the bacterium, lysozyme and protease inhibitors were added at the same time, and stirred at 4° C. for 30 minutes. Then, a suspension was subjected to an ultrasonic treatment at 4° C. for 30 seconds for 5 times. The suspension was collected, and centrifuged at 12000 RCF for 20 minutes. A supernatant was collected, and the supernatant was filtered with a membrane with a pore size of 0.45 μm, and then added with 0.5% NP-40. A protein with the His6 tag was combined with NiNTA metal affinity resin and eluted, and the protein was concentrated and dialyzed. The His6 tag was removed from an EE-RxRα protein by thrombin digestion (10 units of thrombin was added per mg of protein, and incubated at 25° C. for 2 hours). Then, thrombin was removed in batches with anisole agarose gel 6B, and the protein was concentrated and dialyzed. The protein was used in a co-activated peptide recruitment test.

Co-Activated Peptide Recruitment Test of THR-β/RXR/GRIP1

50 mM Hepes, 1 mM DTT, pH 7.0, 0.05% NP40 and 0.2 mg/mL BSA (binding buffer) were prepared into 30 μL of H6-THR-β (50 nM), and then mixed with an equal volume of EE-RxRα (50 nM) buffer. Then, 6 μL of T3 (0 μM to 14.8 μM) or test compound (0 mM to 1.2 mM) was added into DMSO, and the solution was incubated at 37° C. for 30 minutes. Then, 30 μL of binding buffer and 30 μL of biotin-GRIP1 peptide (100 nM) in 5% DMSO were added, and the solution was incubated at 37° C. for 30 minutes. 30 μL of solution containing 12 nM conjugate-coupled anti-6-histidine His antibody and 160 nM APC-coupled streptavidin (50 mM Tris, 100 mM NaCl, pH 7.4 and 0.2 mg/mL BSA) was added, and incubated at 4° C. overnight. An aliquot (35 μL/sample) was transferred to a 384-well black microtiter plate. A HTRF signal was read on a Victor 5 reader (Perkin Elmer Life and Analytical Sciences).

Co-Activated Peptide Recruitment Test of THR-α/RXR/GRIP1

Except that 125 nM H6-THR-α, 125 nM EE-RxRα and 250 nM biotin-GRIP1 were used, the measurement method was basically the same as the co-activated peptide recovery technology of THR-β/RXR/GRIP1 above.

Test Method 2

A method for testing a THR-α/β activation activity of a compound by an in-vitro cell level was as follows.

Compounds were transferred to a 384-well plate by an ECHO liquid workstation, and each compound was diluted by 3 times with 10 gradient concentrations, which was in triplicate. $1.5\times10^4$ DMEM-cultured cells (TR beta-UAS-bla HEK 293T Cells) or $1.0\times10^4$ TR alpha-UAS-bla HEK 293T Cells were placed in the 384-well plate. HEK 293T-TR beta was incubated in an incubator for 16 hours, and HEK 293T-TR alpha was incubated in an incubator for 24 hours. A LiveBLAzer™-FRET B/G (CCF4-AM) substrate was added into the cell plate to detect expression of β-lactamase in cells, and under excitation of 409 nm, a product produced fluorescence with a wavelength of 447 nm. When the β-lactamase was not expressed, under excitation of 409 nm, fluorescence with a wavelength of 520 nm was directly produced through FRET. Combination between the compound and the protein was determined by detecting a ratio of the two kinds of fluorescence (blue/green, 460 nm/530 nm), thus calculating EC50 of the compound. In each experiment, reference compounds triiodothyronine (T3) and MGL3196 would be used as positive controls for the experiment. Calculation of a factor Z (greater than 0.5) would be used for monitoring a stability of each experiment.

II. Test Results

Some test results are summarized in Table 3 by applying the method above.

TABLE 3

| | Detection of TR_LBD agonist | | | | | | |
|---|---|---|---|---|---|---|---|
| | TR_α | | | TR_β | | | |
| Compound (Cpd) ID | TR_α_EC50 (nM) | Maximum activity ratio (A520/A495) | Measurement of cpd/T3 (maximum ratio) | TR_beta_EC50 (nM) | Maximum activity ratio (A520/A495) | Measurement of cpd/T3 (maximum ratio) | α/β |
| T3 | 0.066 | 5.39 | — | 0.161 | 4.15 | — | 0.41 |
| MGL3196 | 566 | 3.49 | 64.7% | 9.661 | 3.6 | 65.7% | 58.59 |
| 1 | 35.32 | 3.83 | 71.1% | 4.957 | 4.02 | 73.4% | 7.13 |
| 2 | >5000 | 1.54 | NA | 153.9 | 1.21 | 22.1% | >32.49 |
| 4 | 581.2 | 1.59 | 29.5% | 51.65 | 1.46 | 26.6% | 11.25 |
| 5 | 1312 | 2.45 | 45.5% | 45.54 | 2.69 | 49.1% | 28.81 |
| 6 | — | — | — | >5000 | NA | NA | NA |
| 7 | >5000 | 1.43 | NA | 13.39 | 1.24 | 22.6% | >374.41 |
| 8 | 55.03 | 2.32 | 43.0% | 5.479 | 2.96 | 54.0% | 10.04 |
| 9 | >5000 | 1.39 | NA | 14.80 | 1.84 | 33.6% | >337.84 |

| | Detection of TR_cell-based agonist | | | | | | |
|---|---|---|---|---|---|---|---|
| | TR_α | | | TR | | | |
| Compound (Cpd) ID | TR_α_EC50 (nM) | Maximum activity ratio | Test cpd/T3 (maximum ratio) | TR_β_EC50 (nM) | Maximum activity ratio (A460/A530) | Measurement of cpd/T3 (maximum ratio) | α/β |
| T3 | 0.055 | 2.2 | — | 0.325 | 0.407 | | |
| MGL3196 | 2766 | 1.34 | 60.9% | 1054 | 0.377 | 6.9% | 2.62 |
| 1 | 4321 | 2.05 | 93.2% | 576.9 | 0.411 | 7.5% | 7.49 |
| 2 | >20000 | 0.35 | NA | >20000 | 0.145 | NA | — |
| 4 | >20000 | 0.4 | NA | >20000 | 0.166 | NA | — |
| 5 | >20000 | 0.42 | NA | >20000 | 0.134 | NA | — |
| 6 | — | — | — | | | | — |
| 7 | >20000 | 0.19 | NA | >20000 | 0.116 | NA | — |
| 8 | 2195 | 0.72 | 32.7% | 595.5 | 0.339 | 6.2% | 3.69 |
| 9 | >20000 | 0.31 | NA | >20000 | 0.204 | NA | — |

In-Vivo Pharmacodynamic Test

I. Test Method:

In the experiment, golden hamsters (80 g to 110 g, 5 weeks old to 6 weeks old, male, Beijing Charles River, License Number SCXK (J) 2016-0011) were fed with high-fat feedstuffs to produce a hyperlipidemia model, then a compound 1 and a MGL3196 positive control drug were given orally, a TG (triglyceride) content in plasma was measured by an automatic biochemical analyzer, and an efficacy of the compound 1 in treating the nonalcoholic fatty liver (NASH) was evaluated according to measurement results.

After successful establishment of the model, the experimental animals were equally divided into 5 groups according to a blood lipid level, comprising:

group 1: a blank control group, with 6 animals, fed with common feedstuffs and administered with a solvent at the same time by 10 mL/kg;

group 2: a model control group, with 8 animals, fed with the high-fat feedstuffs and administered with the solvent at the same time by 10 mL/kg;

group 3: a low-dose group, with 8 animals, fed with the high-fat feedstuffs and administered with a dose of 5 mg/kg by 10 mL/kg;

group 4: a high-dose group, with 8 animals, fed with the high-fat feedstuffs and administered with a dose of 15 mg/kg by 10 mL/kg; and group 5: a positive control group (MGL3196), with 8 animals, fed with the high-fat feedstuffs and administered with the dose of 15 mg/kg by 10 mL/kg.

Administration mode: oral administration was carried out once per day with a time interval of 24 hours for 4 consecutive weeks. During the experiment, the animals were weighed twice per week, and a remaining amount and an adding amount of the feedstuffs were recorded before each blood sampling detection for calculating a food intake of each group of animals during administration.

II. Test Results:

1. Blood TG (triglyceride) index: referring to FIG. 1.

Figure 2:
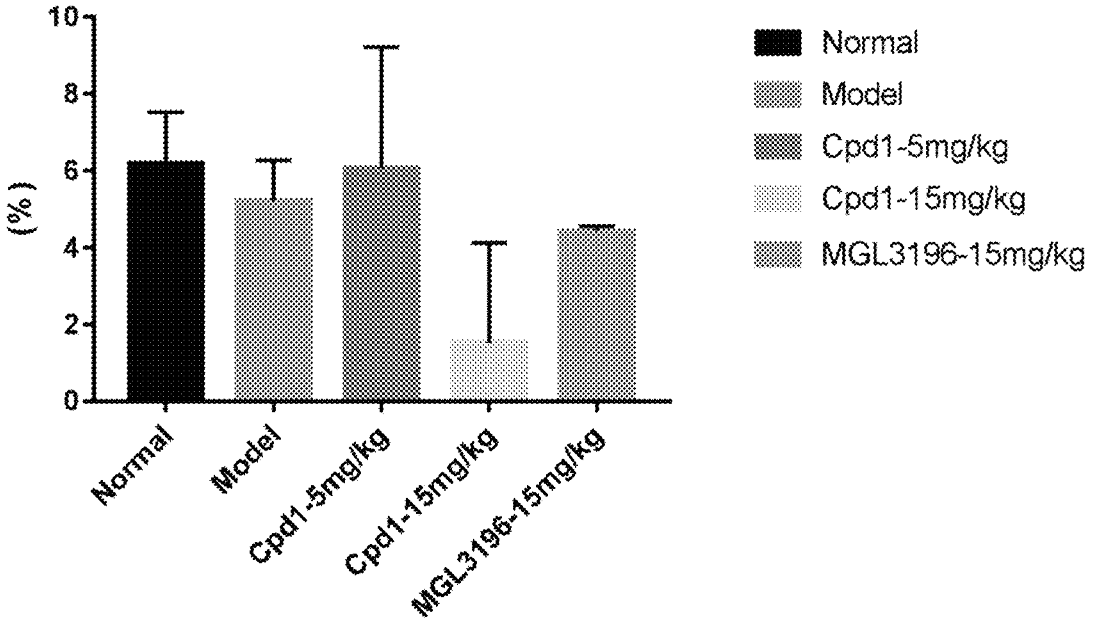
FIG. 2 shows test results of a food utilization rate in the in-vivo pharmacodynamic test.

2. Food utilization rate: referring to FIG. 2.

The food utilization rate represents a weight gain in gram of an animal taking per 100 g of feedstuffs, so that food utilization rate=weight gain (g)/food intake (100 g)×100%. The compound 1 significantly reduces a level of triglyceride in blood compared with the model group during 4 weeks of administration.

The food utilization rate is reduced significantly through the compound 1 (Cpd1), while the food utilization rate is increased to some extent through the MGL3196. It is indicated that the compound 1 can reduce conversion of fat in food into body weight by increasing energy consumption when the same food, especially fat, is taken, which just confirms an action mechanism of the TRβ agonist of the compound 1.

It is indicated that details of specific examples in the present invention are not intended to be construed as a limitation. Various synonyms and modifications may be made without departing from the essence and scope of the present invention, and it is known that these synonymous embodiments are a part of the present invention.

The invention claimed is:

1. A compound with a structure represented by formula (I) or a pharmaceutically acceptable salt, a tautomer, a stereoisomer, a hydrate, or an isotopic derivative thereof:

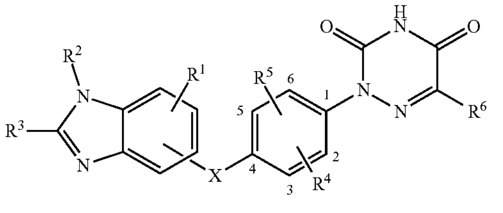

structural formula (I)

wherein, $R^1$ is selected from: H, —CN, —$NO_2$, —$CF_3$, —$OCF_3$, —$CO_2H$, —OH, ethynyl, halogen, amino, alkyl, alkenyl, haloalkyl, haloalkenyl, heteroalkyl, heterocycloalkyl, arylalkyl, cycloalkyl, aryl, heterocycloarylalkyl, heterocycloalkenyl, alkoxy, alkoxyalkyl, alkenyloxy, alkynyl, alkylalkynyl, alkynyloxy, alkylalkynyloxy, alkynyloxy, alkylamino, aminoalkyl, alkylaminocarbonyl, sulfonyl, alkylsulfonyl, alkylsulfinyl, aminosulfonyl, and acyl; and wherein the ethynyl, amino, alkyl, alkenyl, haloalkyl, haloalkenyl, heteroalkyl, heterocycloalkyl, arylalkyl, cycloalkyl, aryl, heterocycloarylalkyl, heterocycloalkenyl, alkoxy, alkoxyalkyl, alkenyloxy, alkynyl, alkylalkynyl, alkynyloxy, alkylalkynyloxy, alkynyloxy, alkylamino, aminoalkyl, alkylaminocarbonyl, sulfonyl, alkylsulfonyl, alkylsulfinyl, aminosulfonyl, and acyl may be substituted by one or more substituents-selected from the group consisting of halogen, —$CF_3$, alkyl, alkenyl, alkynyl, hydroxyl, hydroxyalkyl, alkoxy, alkoxyalkyl, amino, alkylamino, and cycloalkylamino;

$R^2$ is selected from: H, alkyl, alkenyl, haloalkyl, haloalkenyl, heteroalkyl, heterocycloalkyl, arylalkyl, cycloalkyl, aryl, heterocycloaryl, heterocycloarylalkyl, heterocycloalkenyl, alkoxy, alkoxyalkyl, alkylamino, alkylaminocarbonyl, alkynyl, alkylalkynyl, alkynyloxy, alkylalkynyloxy, sulfonyl, alkylsulfonyl, alkylsulfinyl, and aminosulfonyl; and wherein the alkyl, alkenyl, haloalkyl, haloalkenyl, heteroalkyl, heterocycloalkyl, arylalkyl, cycloalkyl, aryl, heterocycloaryl, heterocycloarylalkyl, heterocycloalkenyl, alkoxy, alkoxyalkyl, alkylamino, alkylaminocarbonyl, alkynyl, alkylalkynyl, alkynyloxy, alkylalkynyloxy, sulfonyl, alkylsulfonyl, alkylsulfinyl, and aminosulfonyl may be substituted by one or more substituents selected from the group consisting of halogen, —$CF_3$, alkyl, alkenyl, alkynyl, hydroxyl, hydroxyalkyl, alkoxy, alkoxyalkyl, amino, alkylamino, and cycloalkylamino;

$R^3$ is selected from: H, —CN, —$NO_2$, —$CF_3$, —$OCF_3$, —$CO_2H$, —OH, halogen, amino, alkyl, alkoxy, alkoxyalkyl, heteroalkyl, heterocycloalkyl, arylalkyl, cycloalkyl, heterocycloarylalkyl, heterocycloalkenyl, alkenyloxy, alkynyl, alkylalkynyl, alkynyloxy, alkylalkynyloxy, alkylamino, aminoalkyl, and alkylaminocarbonyl; and wherein the amino, alkyl, alkoxy, alkoxyalkyl, heteroalkyl, heterocycloalkyl, arylalkyl, cycloalkyl, heterocycloarylalkyl, heterocycloalkenyl, alkenyloxy, alkynyl, alkylalkynyl, alkynyloxy, alkylalkynyloxy, alkylamino, aminoalkyl, and alkylaminocarbonyl may be substituted by one or more substituents are selected from the group consisting of halogen, —$CF_3$, alkyl, alkenyl, alkynyl, hydroxyl, hydroxyalkyl, alkoxy, alkoxyalkyl, amino, alkylamino, and cycloalkylamino;

$R^4$ and $R^5$ are each Br, and $R^4$ and $R^5$ are respectively attached to $C_3$- and $C_5$-positions on a corresponding benzene ring;

$R^6$ is —CN; and

X is selected from: covalent bond, —O—, —S—, —NH—, —$SO_2$—, —CONH— or —$(CH_2)q$-, X— is attached to carbon atoms on C4-, C5-, C6- and C7-positions of a benzimidazole ring, and q is 0, 1, 2, and 3.

2. A compound according to claim 1, wherein $R^1$, $R^2$ and $R^3$ are each H.

3. A compound according to claim 1, wherein $R^2$ is methyl.

4. A compound with a structure represented by formula (I) or a pharmaceutically acceptable salt, a tautomer, a stereoisomer, a hydrate or an isotopic derivative thereof:

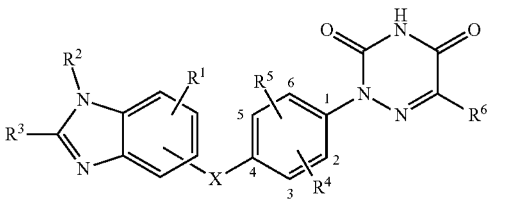

structural formula (I)
wherein, $R^1$ is selected from: H, —CN, —$NO_2$, —$CF_3$, —$OCF_3$, —$CO_2H$, —OH, ethynyl, halogen, amino, alkyl, alkenyl, haloalkyl, haloalkenyl, heteroalkyl, heterocycloalkyl, arylalkyl, cycloalkyl, aryl, heterocycloarylalkyl, heterocycloalkenyl, alkoxy, alkoxyalkyl, alkenyloxy, alkynyl, alkylalkynyl, alkynyloxy, alkylalkynyloxy, alkynyloxy, alkylamino, aminoalkyl, alkylaminocarbonyl, sulfonyl, alkylsulfonyl, alkylsulfinyl, aminosulfonyl, and acyl; and wherein the ethynyl, amino, alkyl, alkenyl, haloalkyl, haloalkenyl, heteroalkyl, heterocycloalkyl, arylalkyl, cycloalkyl, aryl, heterocycloarylalkyl, heterocycloalkenyl, alkoxy, alkoxyalkyl, alkenyloxy, alkynyl, alkylalkynyl, alkynyloxy, alkylalkynyloxy, alkynyloxy, alkylamino, aminoalkyl, alkylaminocarbonyl, sulfonyl, alkylsulfonyl, alkylsulfinyl, aminosulfonyl, and acyl may be substituted by one or more substituents selected from the group consisting of halogen, —$CF_3$, alkyl, alkenyl, alkynyl, hydroxyl, hydroxyalkyl, alkoxy, alkoxyalkyl, amino, alkylamino, and cycloalkylamino;

$R^2$ is selected from: H, alkyl, alkenyl, haloalkyl, haloalkenyl, heteroalkyl, heterocycloalkyl, arylalkyl, cycloalkyl, aryl, heterocycloaryl, heterocycloarylalkyl, heterocycloalkenyl, alkoxy, alkoxyalkyl, alkylamino, alkylaminocarbonyl, alkynyl, alkylalkynyl, alkynyloxy, alkylalkynyloxy, sulfonyl, alkylsulfonyl, alkylsulfinyl, and aminosulfonyl; and wherein the alkyl, alkenyl, haloalkyl, haloalkenyl, heteroalkyl, heterocycloalkyl, arylalkyl, cycloalkyl, aryl, heterocycloaryl, heterocycloarylalkyl, heterocycloalkenyl, alkoxy, alkoxyalkyl, alkylamino, alkylaminocarbonyl, alkynyl, alkylalkynyl, alkynyloxy, alkylalkynyloxy, sulfonyl, alkylsulfonyl, alkylsulfinyl, and aminosulfonyl may be substituted by one or more substituents selected from the group consisting of halogen, —$CF_3$, alkyl, alkenyl, alkynyl, hydroxyl, hydroxyalkyl, alkoxy, alkoxyalkyl, amino, alkylamino, and cycloalkylamino;

$R^3$ is selected from: H, —CN, —$NO_2$, —$CF_3$, —$OCF_3$, —$CO_2H$, —OH, halogen, amino, alkyl, alkoxy, alkoxyalkyl, heteroalkyl, heterocycloalkyl, arylalkyl, cycloalkyl, heterocycloarylalkyl, heterocycloalkenyl, alkenyloxy, alkynyl, alkylalkynyl, alkynyloxy, alkylalkynyloxy, alkylamino, aminoalkyl, and alkylaminocarbonyl; and wherein the amino, alkyl, alkoxy, alkoxyalkyl, heteroalkyl, heterocycloalkyl, arylalkyl, cycloalkyl, heterocycloarylalkyl, heterocycloalkenyl, alkenyloxy, alkynyl, alkylalkynyl, alkynyloxy, alkylalkynyloxy, alkylamino, aminoalkyl, and alkylaminocarbonyl may be substituted by one or more substituents selected from the group consisting of halogen, —$CF_3$, alkyl, alkenyl, alkynyl, hydroxyl, hydroxyalkyl, alkoxy, alkoxyalkyl, amino, alkylamino, and cycloalkylamino;

$R^6$ is —CN;

X is selected from: covalent bond, —O—, —S—, —NH—, —$SO_2$—, —CONH— or —$(CH_2)$q-, X— is attached to carbon atoms on $C_4$-, $C_5$-, $C_6$- and $C_7$-positions of a benzimidazole ring, and q is 0, 1, 2, and 3; and $R^4$ and $R^5$ are each difluoromethyl, and $R^4$ and $R^5$ are respectively attached to $C_3$- and $C_5$-positions on a corresponding benzene ring.

5. A compound with a structure represented by formula (I) or a pharmaceutically acceptable salt, a tautomer, a stereoisomer, a hydrate or an isotopic derivative thereof:

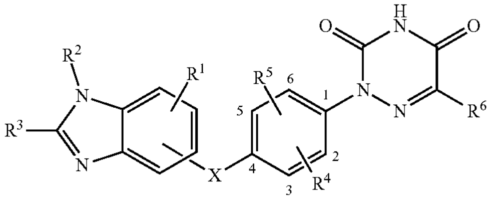

structural formula (I)
wherein, $R^1$ is selected from: H, —CN, —$NO_2$, —$CF_3$, —$OCF_3$, —$CO_2H$, —OH, ethynyl, halogen, amino, alkyl, alkenyl, haloalkyl, haloalkenyl, heteroalkyl, heterocycloalkyl, arylalkyl, cycloalkyl, aryl, heterocycloarylalkyl, heterocycloalkenyl, alkoxy, alkoxyalkyl, alkenyloxy, alkynyl, alkylalkynyl, alkynyloxy, alkylalkynyloxy, alkynyloxy, alkylamino, aminoalkyl, alkylaminocarbonyl, sulfonyl, alkylsulfonyl, alkylsulfinyl, aminosulfonyl, and acyl; and wherein the ethynyl, amino, alkyl, alkenyl, haloalkyl, haloalkenyl, heteroalkyl, heterocycloalkyl, arylalkyl, cycloalkyl, aryl, heterocycloarylalkyl, heterocycloalkenyl, alkoxy, alkoxyalkyl, alkenyloxy, alkynyl, alkylalkynyl, alkynyloxy, alkylalkynyloxy, alkynyloxy, alkylamino, aminoalkyl, alkylaminocarbonyl, sulfonyl, alkylsulfonyl, alkylsulfinyl, aminosulfonyl, and acyl may be substituted by one or more substituents selected from the group consisting of halogen, —$CF_3$, alkyl, alkenyl, alkynyl, hydroxyl, hydroxyalkyl, alkoxy, alkoxyalkyl, amino, alkylamino, and cycloalkylamino;

$R^2$ is selected from: H, alkyl, alkenyl, haloalkyl, haloalkenyl, heteroalkyl, heterocycloalkyl, arylalkyl, cycloalkyl, aryl, heterocycloaryl, heterocycloarylalkyl, heterocycloalkenyl, alkoxy, alkoxyalkyl, alkylamino, alkylaminocarbonyl, alkynyl, alkylalkynyl, alkynyloxy, alkylalkynyloxy, sulfonyl, alkylsulfonyl, alkylsulfinyl, and aminosulfonyl; and wherein the alkyl, alkenyl, haloalkyl, haloalkenyl, heteroalkyl, heterocycloalkyl, arylalkyl, cycloalkyl, aryl, heterocycloaryl, heterocycloarylalkyl, heterocycloalkenyl, alkoxy, alkoxyalkyl, alkylamino, alkylaminocarbonyl, alkynyl, alkylalkynyl, alkynyloxy, alkylalkynyloxy, sulfonyl, alkylsulfonyl, alkylsulfinyl, and aminosulfonyl may be substituted by one or more substituents selected from the group consisting of halogen, —$CF_3$, alkyl, alkenyl, alkynyl, hydroxyl, hydroxyalkyl, alkoxy, alkoxyalkyl, amino, alkylamino, and cycloalkylamino;

$R^3$ is selected from: H, —CN, —$NO_2$, —$CF_3$, —$OCF_3$, —$CO_2H$, —OH, halogen, amino, alkyl, alkoxy, alkoxyalkyl, heteroalkyl, heterocycloalkyl, arylalkyl, cycloalkyl, heterocycloarylalkyl, heterocycloalkenyl, alkenyloxy, alkynyl, alkylalkynyl, alkynyloxy, alkylalkynyloxy, alkylamino, aminoalkyl, and alkylaminocarbonyl; and wherein the amino, alkyl, alkoxy, alkoxyalkyl, heteroalkyl, heterocycloalkyl, arylalkyl, cycloalkyl, heterocycloarylalkyl, heterocycloalkenyl, alkenyloxy, alkynyl, alkylalkynyl, alkynyloxy, alkylalkynyloxy, alkylamino, aminoalkyl, and alkylaminocarbonyl may be substituted by one or more substituents selected from the group consisting of halogen, —$CF_3$, alkyl, alkenyl, alkynyl, hydroxyl, hydroxyalkyl, alkoxy, alkoxyalkyl, amino, alkylamino, and cycloalkylamino;

$R^6$ is —CN;

X is selected from: covalent bond, —O—, —S—, —NH—, —$SO_2$—, —CONH— or —$(CH_2)q$-, X— is attached to carbon atoms on $C_4$-, $C_5$-, $C_6$- and $C_7$-positions of a benzimidazole ring, and q is 0, 1, 2, and 3; and $R^4$ and $R^5$ are each trifluoromethyl, and $R^4$ and $R^5$ are respectively attached to $C_3$- and $C_5$-positions on a corresponding benzene ring.

6. A compound which is selected from the following compounds and pharmaceutically acceptable salts thereof:

1

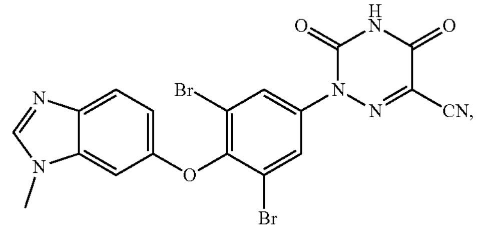

3

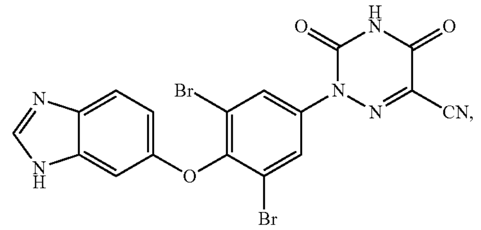

4

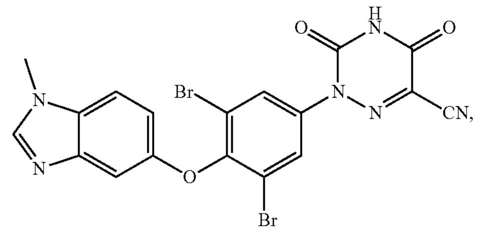

-continued

10

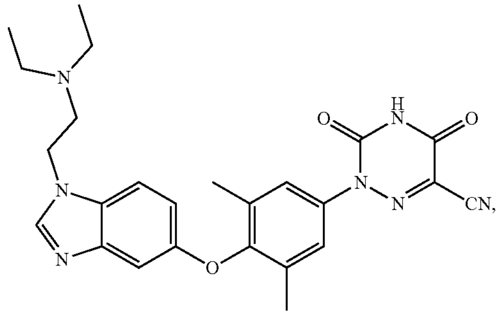

11

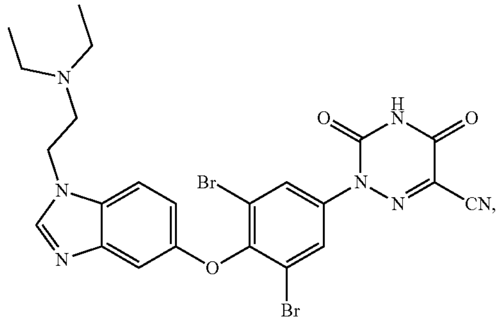

12

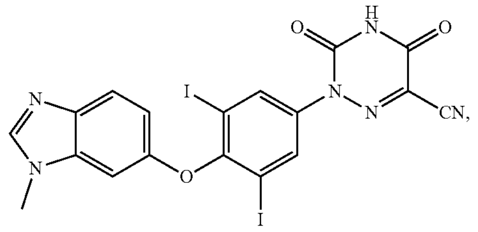

13

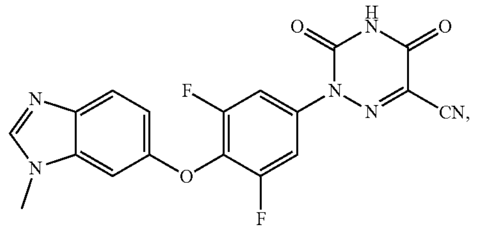

14

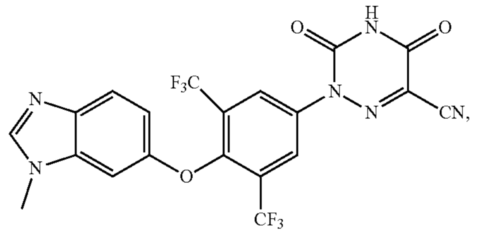

15

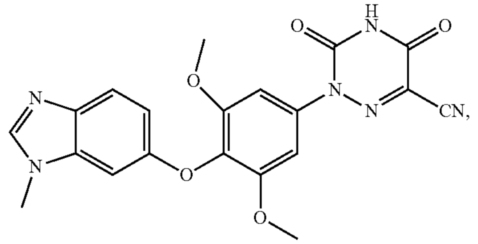

-continued

16

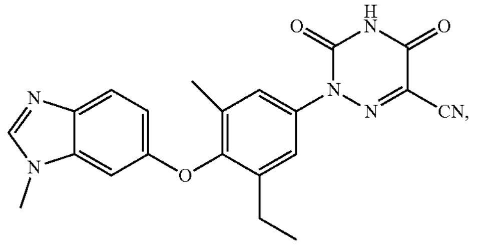

17

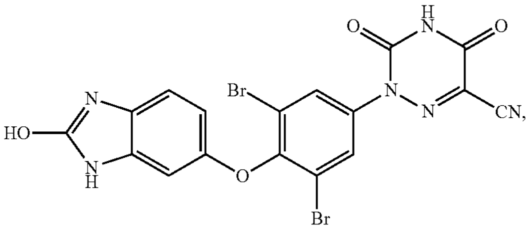

18

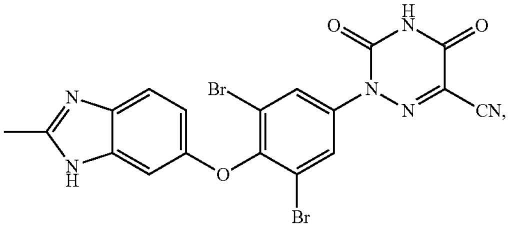

19

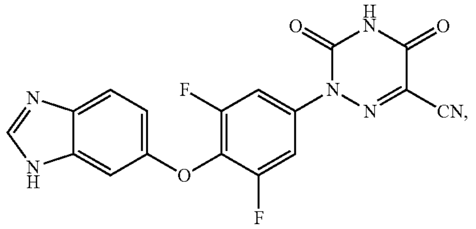

20

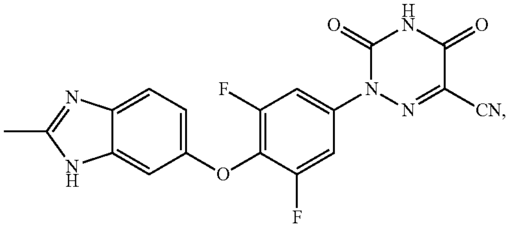

-continued

21

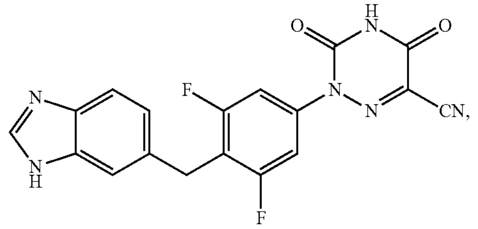

22

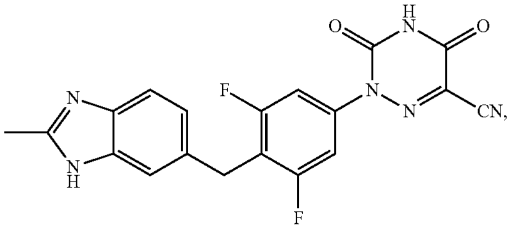

and

24

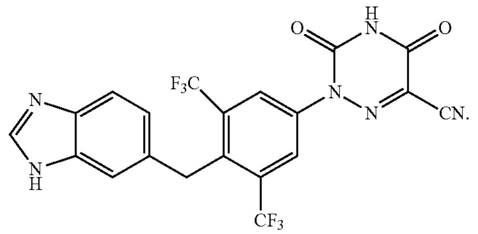

7. A method for treating obesity, diabetes, NASH (non-alcoholic steatohepatitis), hypothyroidism, or thyroid cancer regulated by a thyroid hormone, or for treating hyperlipidemia or atherosclerosis regulated by a thyroid hormone, or for treating hypercholesterolemia regulated by a thyroid hormone, comprising administering a therapeutically effective amount of the compound according to claim 1.

* * * * *